United States Patent [19]
Behr et al.

[11] Patent Number: 5,852,148
[45] Date of Patent: Dec. 22, 1998

[54] PERFLUOROALKYL HALIDES AND DERIVATIVES

[75] Inventors: Frederick E. Behr, Woodbury, Minn.; Rudolf J. Dams, Zwijndrecht; Johan E. DeWitte, Moerbeeklaan, both of Belgium; Donald F. Hagen, Woodbury, Minn.

[73] Assignee: Minnesota Mining & Manufacturing Company, St. Paul, Minn.

[21] Appl. No.: 794,828

[22] Filed: Feb. 4, 1997

Related U.S. Application Data

[60] Continuation-in-part of Ser. No. 489,094, Jun. 9, 1995, abandoned, which is a division of Ser. No. 314,939, Sep. 29, 1994, abandoned, which is a continuation of Ser. No. 728,184, Jul. 10, 1991, abandoned.

[51] Int. Cl.⁶ .................................................. C08F 18/20
[52] U.S. Cl. .......................... 526/245; 526/243; 428/500
[58] Field of Search .................................. 526/245, 243; 428/500

[56] References Cited

U.S. PATENT DOCUMENTS

| | | |
|---|---|---|
| 2,519,983 | 8/1950 | Simons . |
| 2,567,011 | 9/1951 | Diesslin et al. . |
| 2,666,797 | 1/1954 | Husted et al. . |
| 2,691,043 | 10/1954 | Husted et al. . |
| 2,732,398 | 1/1956 | Brice et al. . |
| 2,759,019 | 8/1956 | Brown et al. . |
| 2,764,602 | 9/1956 | Ahlbrecht . |
| 2,803,656 | 8/1957 | Ahlbrecht et al. . |
| 2,950,317 | 8/1960 | Brown et al. . |
| 2,972,638 | 2/1961 | Tiers . |
| 3,094,547 | 6/1963 | Heine . |
| 3,283,012 | 11/1966 | Day . |
| 3,398,182 | 8/1968 | Guenthner et al. . |
| 3,420,877 | 1/1969 | Pavlik . |
| 3,499,940 | 3/1970 | Katsushima et al. . |
| 3,525,758 | 8/1970 | Katsushima et al. . |
| 3,532,659 | 10/1970 | Hager et al. . |
| 3,532,674 | 10/1970 | Banitt et al. . |
| 3,540,126 | 11/1970 | Chang et al. . |
| 3,562,156 | 2/1971 | Francen . |
| 3,919,361 | 11/1975 | Katsushima et al. . |
| 4,024,178 | 5/1977 | Landucci . |
| 4,127,711 | 11/1978 | Lore et al. . |
| 4,158,672 | 6/1979 | Dear et al. . |
| 4,167,639 | 9/1979 | Billenstein et al. . |
| 4,219,681 | 8/1980 | Schwenk et al. . |
| 4,359,096 | 11/1982 | Berger . |
| 4,484,990 | 11/1984 | Bultman et al. . |
| 4,489,006 | 12/1984 | Krahler . |
| 4,540,497 | 9/1985 | Chang et al. . |
| 4,606,737 | 8/1986 | Stern . |
| 4,668,406 | 5/1987 | Chang . |
| 5,091,550 | 2/1992 | Falk et al. . |
| 5,132,445 | 7/1992 | Falk et al. . |
| 5,151,535 | 9/1992 | Fuchikami et al. . |
| 5,260,492 | 11/1993 | Feiring et al. . |
| 5,326,917 | 7/1994 | Feiring et al. . |
| 5,350,878 | 9/1994 | Caporiccio . |

FOREIGN PATENT DOCUMENTS

| | | |
|---|---|---|
| 0 142 041 A1 | 5/1985 | European Pat. Off. . |
| 0 275 771 | 7/1988 | European Pat. Off. . |
| 61-209286 | 9/1986 | Japan . |
| 62-38419 | 2/1987 | Japan . |
| 64-45411 | 2/1989 | Japan . |
| 5-32712 | 2/1993 | Japan . |
| 904263 | 8/1962 | United Kingdom . |
| 2 199 828 | 7/1988 | United Kingdom . |

OTHER PUBLICATIONS

3M Company trade bulletin 98–0211–2213–4 (38.3) BPH, issued Mar., 1988.

Banks R.E., Ed., "Organofluorine Chemicals and their Industrial Applications," Ellis Horwood, Ltd., Chichester, England, 1979 pp. 213–234.

Bernett, M.K. and Zisman, W.A., "Surface Properties of Perfluoro Acids as Affected by Terminal Branching and Chlorine Substitution," J. Phys. Chem., 71, 1967, pp. 2075–2082.

The Journal of Organic Chemistry, vol. 23, "Applicability of the Arndt–Eistert Reaction to Fluorinated Acids and Their Derivatives", 1958, pp. 1166–1169.

The Journal of Organic Chemistry, vol. 53, No. 24, "Electrochemical oxidation of Polyfluoroalkyl Iodides: Direct Anodic Transformation of $C_8F_{17}CH_2CH_2I$ to Amides, Esters, and Ethers," 1988, pp. 5714–5720.

Journal of Fluorine Chemistry, vol. 43, No. 2, "Synthesis of Fluorine–Containing Nitro Compounds," 1989, pp. 291–300.

Park, J.D. et al, "Free–Radical Catalyzed Addition of Unsaturated Alcohols to Perhaloalkanes," 1961 pp. 2089–2095.

Primary Examiner—Jeffrey T. Smith
Assistant Examiner—N. Sarofim
Attorney, Agent, or Firm—John A. Fortkort

[57] ABSTRACT

Novel mixtures of perfluoroalkyl halides and derivatives thereof are described. These mixtures contain some compounds with a straight perfluoroalkyl group and some with a branched perfluoroalkyl group. Methods of preparation and use are also described.

42 Claims, No Drawings

PERFLUOROALKYL HALIDES AND DERIVATIVES

RELATED APPLICATIONS

This application is a Continuation-In-Part of Ser. No. 08/489,094, filed Jun. 9, 1995, now abandoned; which was a Divisional of Ser. No. 08/314,939, filed Sep. 29, 1994, now abandoned; which was a Continuation of 07/728,184, filed Jul. 10, 1991, now abandoned.

FIELD OF THE INVENTION

This invention relates to perfluoroalkyl halides and derivatives thereof, and to the preparation and use of such halides and derivatives in imparting water and oil repellency to substrates.

BACKGROUND OF THE INVENTION

Fluorocarbon derivatives (sometimes called organofluorine compounds or fluorochemicals) are a class of substances containing portions which are fluorocarbon in nature, e.g. hydrophobic, oleophobic, and chemically inert, and portions which are organic or hydrocarbon in nature, e.g. chemically reactive in organic reactions. The class includes some substances which are familiar to the general public, such as those which give oil and water repellency and stain and soil resistance to textiles, e.g. Scotchgard™ carpet protector. Other substances of the class have various industrial uses, such as reducing the surface tension of liquids, reducing evaporation and flammability of volatile organic liquids, and improving the leveling of organic polymer coatings. Examples of industrial substances are the Fluorad™ fluorochemical surfactants described in 3M Company trade bulletin 98-0211-2213-4 (38.3) BPH, issued March, 1988.

Conventional fluorochemicals can be prepared from precursors such as fluoroalkyl iodides, fluoroalkyl carboxylic acid fluorides, and fluoroalkyl sulfonyl fluorides. See for example, "Organofluorine Chemicals and Their Industrial Applications", R. E. Banks, Ed., Ellis Horwood, Ltd., Chichester, England, 1979, pp. 214–234.

Some perfluoroalkyl iodides can be prepared by telomerization of $C_2F_5I$ or $(CF_3)_2CFI$ with $C_2F_4$ yielding $C_2F_5(C_2F_4)_nI$ or $(CF_3)_2CF(CF_2CF_2)_nI$, respectively, where n is typically from 1 to 4. See R. E. Banks, supra. All of the perfluoroalkyl iodides obtained from $(CF_3)_2CFI$ contain perfluoroalkyl groups with a terminal branch, and such branched-chain perfluoroalkyl groups will hereinafter be represented by "$R_{fb}$". All of the perfluoroalkyl iodides obtained from $C_2F_5I$ contain straight-chain perfluoroalkyl groups without branches, and such straight-chain (or "linear") perfluoroalkyl groups will hereinafter be represented by "$R_{fs}$". For brevity, "$R_f$" will hereinafter be used to represent a perfluoroalkyl group with either a straight or a branched-chain. Perfluoroalkyl iodides can be converted into other functional (or reactive) materials, for example by the following illustrative schemes.

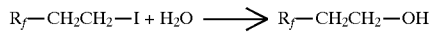

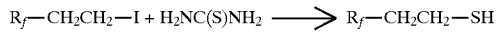

The alcohol, thiol, and olefin derivatives of the above schemes can be further converted to a great variety of derivatives, e.g., acrylates and polymers thereof, sulfates and salts thereof, carboxylic acids and esters thereof, etc. These further derivatives retain the original structure of the $R_f$ group, that is, the $R_f$ group remains either straight or branched.

Functional materials derived from telomer iodides will (as stated above) contain either 100% straight-chain ($R_{fs}$) or 100% branched-chain ($R_{fb}$) perfluoroalkyl groups. Contradictory data have been reported in the literature regarding the relative advantage of straight-chain versus branched-chain perfluoroalkyl groups. In U.S. Pat. No. 4,127,711 (Lore et al.) perfluoroalkyl straight-chains are said to be preferred for textile applications, whereas in U.S. Pat. No. 3,525,758 (Katsushima et al.) it is disclosed that surfactants containing 100% branched-chain perfluoroalkyl groups are more effective than surfactants containing straight-chain perfluoroalkyl groups in lowering the surface tension of aqueous solutions. However, it has generally been accepted that among fluorinated surfactants of the same carbon number, straight-chain products generally give lower surface tension in aqueous solutions. Banks, supra at 222–223, describes that, except at very low concentrations (less than 0.01% or 100 ppm), lower surface tension is attained with straight-chain fluorochemicals. Additionally, an article written by Bennett and Zismann (J. Phys. Chem., 71, 1967, p. 2075–2082) discloses that a condensed monolayer of a fully fluorinated straight-chain alkanoic acid has a lower critical surface energy than its terminally branched analogue with the same chain length.

In addition to the telomerization procedure described above, another method of producing many fluorochemicals or their precursors is the fluorination process commercialized initially in the 1950s by 3M Company, which comprises passing an electric current through a mixture of the organic starting compound and liquid anhydrous hydrogen fluoride. This fluorination process is commonly referred to as "electrochemical fluorination" or "ECF". Some early patents describing such technology include U.S. Pat. Nos. 2,519,983 (Simons), 2,567,011 (Diesslin et al.), 2,666,797 (Husted et al.), 2,691,043 (Husted et al.), and 2,732,398 (Brice et al.); they describe the preparation of such fluorochemical compounds as perfluoroalkyl carbonyl fluorides, e.g. $C_4F_9$—COF, and perfluoroalkyl sulfonyl fluorides, e.g. $C_4F_9$—$SO_2F$, and derivatives thereof.

When perfluoroalkyl carbonyl fluorides and perfluoroalkyl sulfonyl fluorides are prepared by electrochemical fluorination (ECF) of appropriate hydrocarbon precursors, the resulting products are mixtures of compounds, where some of said compounds contain a straight-chain perfluoroalkyl group, e.g., $R_{fs}$—$SO_2F$, and others of said compounds contain a branched-chain perfluoroalkyl group, e.g., $R_{fb}$—$SO_2F$. Such mixtures of compounds result even when the starting materials contain only compounds with straight-chain alkyl groups. Such mixtures of compounds, e.g. a mixture of $R_{fs}$—$SO_2F$ and $R_{fb}$—$SO_2F$, can be represented, for brevity, by the formula, $R_{fsb}$—SO2F, which formula represents a mixture of compounds. The "sb" subscripts indicate that the formula represents a mixture of compounds, that is, a mixture of $R_{fs}$—$SO_2F$ and $R_{fb}$—$SO_2F$.

ECF-derived acid fluorides can be converted into other functional materials, for example by the following illustrative schemes.

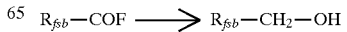   dihydro derivatives

-continued

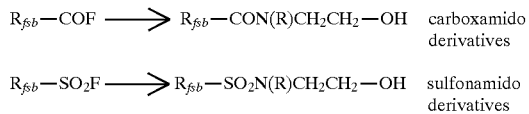

Each $R_{fsb}$ containing formula, e.g., $R_{fsb}$—COF, represents ECF derived mixtures which contain some compounds with a straight-chain perfluoroalkyl group and other compounds with a branched-chain perfluoroalkyl group.

U.S. Pat. No. 2,950,317 (Brown et al) describes a process for the preparation of fluorocarbon sulfonyl chlorides from the corresponding fluorocarbon sulfonyl fluorides.

An article by Park et al. (23, J. Org. Chem, 1166–1169 (1958)) describes the preparation of certain fluorochemical compounds with three or less fully-fluorinated carbon atoms. Compounds described include n—C3F$_7$—CH$_2$CH$_2$—I and n—C3F$_7$—CH$_2$—CO$_2$H.

SUMMARY OF THE INVENTION

Briefly, the present invention, in one aspect, provides novel fluorochemical compositions which comprise a mixture of perfluoroalkyl halide compounds. Some of the perfluoroalkyl halide compounds of the mixture contain a straight-chain group (the term "straight-chain" is used herein in its accepted sense to mean normal or unbranched perfluoroalkyl group, e.g., CF$_3$CF$_2$CF$_2$CF$_2$—), and some contain a branched-chain perfluoroalkyl group (e.g., (CF$_3$)$_2$CFCF$_2$—).

The perfluoroalkyl halide compounds comprise a perfluoroalkyl group, a halogen atom selected from the group consisting of Cl, Br, and I, and a fluorine-free alkylene linking group bonded to the perfluoroalkyl group and to the halogen atom.

The alkylene linking group contains at least two catenary carbon atoms, one of which is bonded to the perfluoroalkyl group, and the other of which is bonded to the halogen atom (e.g., as in R$_{fsb}$—CH$_2$CH$_2$—I, but not as in R$_{fsb}$—CH(CH$_3$)—I). The carbon atom of the alkylene linking group which is directly bonded to the perfluoroalkyl group will be referred to as the alpha carbon atom, and the catenary carbon atom of the alkylene linking group which is bonded to said alpha carbon atom will be referred to as the "beta carbon atom". Such α and β carbon atoms are illustrated, for example, in the formula

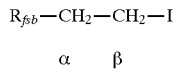

In another aspect, this invention provides novel fluorochemical compositions which comprise a mixture of perfluoroalkyl derivative compounds of said perfluoroalkyl halide compounds. Some of said perfluoroalkyl derivative compounds of said mixture contain a straight-chain perfluoroalkyl group, e.g., CF$_3$CF$_2$CF$_2$CF$_2$—, and some contain a branched-chain perfluoroalkyl group, e.g., (CF$_3$)$_2$CFCF$_2$—. Said derivatives are obtained from said halides by one or more steps, and retain from the precursor halides the perfluoroalkyl group and the alpha and beta carbon atoms of the linking group. One or both of said alpha and beta carbon atoms may be converted, for example, to a carbonyl (C=O) or alkenylene carbon atom (C=C), but they are always retained in some form in the derivative.

In still another aspect, the present invention provides novel fluoropolymers having both straight chain and branched chain pendant perfluoroalkyl groups. These fluoropolymers may be made, for example, through the polymerization of monomers having both branched and straight chain pendant perfluoroalkyl groups, or through the copolymerization of a first monomeric species having straight chain pendant perfluoroalkyl groups with a second monomeric species having branched chain pendant perfluoroalkyl groups (in the latter method, the ratio of the first monomeric species to the second monomeric species will preferably be within the range of about 1.5:1 to about 9:1, and more preferably within the range of about 2:1 to about 6:1). The monomeric species may be polymerized before or after being applied to a substrate. Preferably, about 60 to about 90% of the pendant perfluoroalkyl groups in the polymer are straight chain and about 10 to about 40% of the perfluoroalkyl groups in the polymer are branched chain, and more preferably, about 60 to about 90% of the pendant perfluoroalkyl groups in the polymer are straight chain and about 10 to about 40% of the perfluoroalkyl groups are branched chain. The fluoropolymers of the present invention form better emulsifications, and exhibit better physical properties (e.g., improved solubility, better oil repellency and higher spray ratings) than the corresponding polymers having only straight chain or only branched chain pendant perfluoroalkyl groups.

DETAILED DESCRIPTION OF THE INVENTION

Preferably, the compositions of this invention comprise a mixture of compounds wherein 50 to 95% of said compounds contain a straight-chain perfluoroalkyl group (R$_{fs}$), and wherein 5 to 50% of said compounds contain a branched-chain perfluoroalkyl group (R$_{fb}$). Most preferably, the compositions of this invention comprise a mixture of compounds wherein 60 to 90% of said compounds contain a straight-chain perfluoroalkyl group (R$_{fs}$), and wherein 10 to 40% of said compounds contain a branched-chain perfluoroalkyl group (R$_{fb}$).

The compositions of this invention also may contain mixtures of compounds such that the number of carbon atoms in the perfluoroalkyl groups are predominately, e.g., greater then 70%, of one length, for example where greater then 70% of all perfluoroalkyl groups in the mixture of compounds have 8 carbon atoms.

Because of the wide variety of the fluorochemical compositions of this invention, they can be used in numerous applications, including those where conventional fluorochemicals are used. Such applications are described, for example, in Banks, supra, which descriptions are incorporated herein. The fluorochemical compositions of this invention are useful in improving or imparting properties to solutions and substrates such as wetting, penetration, spreading, leveling, foaming, foam stabilization, flow properties, emulsification, dispersability, and oil, water, and soil repellency.

A class of the fluorochemical compositions of this invention comprises a mixture of perfluoroalkyl halide compounds which mixture can be represented by Formula I.

      I.

In Formula I, the "fsb" subscript is meant to indicate that Formula I represents a mixture of compounds, that is, a mixture of R$_{fs}$—CH$_2$CH(R$^1$)R$^2$—X and R$_{fb}$—CH$_2$CH(R$^1$)R$^2$—X. Some of said compounds contain a straight-chain perfluoroalkyl group (R$_{fs}$) and all others of said compounds contain a branched-chain perfluoroalkyl group (R$_{fb}$).

In Formula I, $R_{fsb}$ is a perfluoroalkyl group. Said perfluoroalkyl group is saturated, mono-valent, and has at least 4 fully-fluorinated carbon atoms. While the perfluoroalkyl group can contain a large number of carbon atoms, compounds where the perfluoroalkyl group is not more than 20 carbon atoms will be adequate and preferred since larger radicals usually represent a less efficient utilization of the fluorine (lower fluorine efficiency) than is obtained with shorter chains. Perfluoroalkyl groups containing from about 4 to about 10 carbon atoms are most preferred.

In Formula I, $R^1$ is a lower alkyl group, e.g., with 1 to 4 carbon atoms, or an aromatic group, e.g., phenyl, or combinations thereof, e.g., tolyl. $R^1$ may also contain hereto atoms, e.g., S, O, N, Si, for example $R^1$ may be —CH$_2$—OH.

In Formula I, $R^2$ is a covalent bond or an alkylene group such as (CH$_2$)m, where m is from 1 to 20, or —CH(R) where R is as defined for $R^1$, and $R^2$ may also contain said hereto atoms.

In Formula I, the carbon atom bonded to the perfluoroalkyl group may be referred to as the alpha carbon atom and is represented in Formula I as the "C" in CH$_2$. The other depicted carbon atom, which is bonded to the alpha carbon atom, may be referred to as the beta carbon atom and is represented in Formula I as the "C" in CH(R$^1$).

In Formula I, X is I, Cl, or Br.

A subclass of the fluorochemical compositions of this invention comprises a mixture of perfluoroalkyl halide compounds which mixture can be represented by Formula II.

$$R_{fsb}-(CH_2CH_2)_n-X \qquad II$$

In Formula II, $R_{fsb}$ and X are as described above for Formula I and n is an integer from 1 to 5.

The perfluoroalkyl halide mixtures of this invention are reactive chemicals and can be converted into their reactive or functional derivatives by one or more steps. A class of such derivatives can be represented by the formula $R_{fsb}$—Z where $R_{fsb}$ is as defined and described above and Z is an organic moiety or an oxygen-containing inorganic moiety that is a one-step or multi-step derivative of the halide compounds. Various functional embodiments of Z make the derivatives useful reagents for the introduction of the $R_{fsb}$ moiety into molecules. Z can be an organic functional moiety, i.e., one which contains one or more carbon atoms, such as carbonyl-containing, sulfonyl-containing, alkylene-containing, nitrogen-containing, and oxygen-containing moieties or Z can be an oxygen-containing inorganic moiety, such as sulfonyl-containing and sulfonyloxy-containing moieties. Representative functional Z moieties are, for example, polymerizable groups which will undergo electrophilic, nucleophilic, or free radical reaction, derivatives with such groups being useful to form polymers comprising polymeric chains having a plurality of pendant perfluroalkyl groups. Derivative compounds of this invention include carboxylic and sulfonic acids and their metal and ammonium salts, esters, including alkyl and alkenyl esters, amides, tetrahydroalcohols (—C$_2$H$_4$OH), esters of tetrahydro-alcohols, acrylates (and polyacrylates), mercaptans, alkenyl ethers, etc. Stated otherwise, Z in the above formulas can contain —COOH, —COOM$_{1/v}$, —COONH$_4$, —CH$_2$COOR, —CONH$_2$, —COONR$^1$R$^2$, —NR$^1$R$^2$, —CONR$^1$R$^3$A, —CH$_2$OH,

—CF$_2$OCF(CF$_3$)COF, —CH$_2$NCO, —CH$_2$SH, —CN, —SO$_3$H, —SO$_3$M$_{1/v}$, —SO$_3$NH$_4$, —SO$_2$NR$^1$R$^2$, —SO$_2$NR$^1$R$^3$A, —SO$_2$NH$_2$, —SO$_3$R, —CH$_2$SH, —CH$_2$NR$^1$R$^2$, —CH$_2$OCOCR$^4$=CH$_2$, CH$_2$OCOCF$_2$SF$_5$, and the like, where M is a metal atom having a valence "v", such as a monovalent metal atom like K or Na; R is alkyl (e.g. with 1 to 14 carbon atoms), aryl (e.g. with 6 to 10 or 12 ring carbon atoms), or a combination thereof (e.g. alkaryl or aralkyl); $R^1$ and $R^2$ are each independently H or R; $R^3$ is alkylene (e.g. with 1 to 13 carbon atoms; $R^4$ is H or CH$_3$; A is an aliphatic or aromatic moiety, which can contain a carboxy or sulfo group or an alkali metal or ammonium salt or ester thereof, a carboxamido, a sulfonamido, or contain 1 to 3 hydroxy groups, 1 or more ether-oxygen or oxirane-oxygen atoms, a cyano group, a phosphono group, or one or more primary, secondary, or tertiary amine groups, or quaternized amine group, or other functional group.

The above illustrated derivatives can be converted to other derivative fluorochemical compositions of this invention. For example, hydroxy functional derivatives can be converted to corresponding sulfate derivatives useful as surfactants as described, for example, in U.S. Pat. No. 2,803,656 (Ahlbrecht et al.) or phosphate derivatives useful as textile and leather treating agents as described, for example, in U.S. Pat. No. 3,094,547 (Heine). Hydroxy functional derivatives can also be reacted with isocyanates to make carbamato-containing derivatives such as urethanes, carbodiimides, biurets, allophanates, and quanidines useful in treating fibrous substrates such as textiles as described, for example, in U.S. Pat. Nos. 3,398,182 (Guenthner et al.), 4,024,178 (Landucci), 4,668,406 (Chang), 4,606,737 (Stern), and 4,540,497 (Chang et al.), respectively.

Amine functional derivatives can be converted to corresponding amine salts useful as surfactants, as described, for example, in U.S. Pat. Nos. 2,764,602 (Ahlbrecht), 2,759,019 (Brown et al.) or amphoteric surfactants as described, for example, in U.S. Pat. No. 4,484,990 (Bultman et al.). Amine functional derivative can be successively reacted to form an amphoteric surfactant as described, for example, in U.S. Pat. No. 4,359,096 (Berger) (see Table I thereof).

The polymerizable functional derivatives of this invention can be used to make polymers such as polyacrylates, polyesters, polyurethanes, polyamides, and polyvinyl ethers. Such polymers can be made by conventional step-growth, chain-growth, or graft polymerization techniques or processes. The step-growth polymers can be made, for example, from those derivatives having hydroxyl, carboxyl, isocyanato, or amino polymerizable groups. The acrylate, methacrylate, or vinyl derivatives of this invention can be used to make chain-growth polymers, such as polyacrylates. Fluorochemical ethylenically unsaturated monomers of this invention can be homopolymerized to make homopolymers, or copolymerized with copolymerizable monomers to make random, alternating, block, and graft polymers. Copolymerizable monomers which can be used include fluorine-containing and fluorine-free (or hydrocarbon) monomers, such as methyl methacrylate, ethyl acrylate, butyl acrylate, octadecylmethacrylate, acrylate and methacrylate esters of poly(oxyalkylene) polyol oligomers and polymers, e.g., poly (oxyethylene) glycol dimethacrylate, glycidyl methacrylate, ethylene, vinyl acetate, vinyl chloride, vinylidene chloride, vinylidene fluoride, acrylonitrile, vinyl chloroacetate, isoprene, chloroprene, styrene, butadiene, vinylpyridine, vinyl alkyl ethers, vinyl alkyl ketones, acrylic and methacrylic acid, 2-hydroxyethyl acrylate, N-methylolacrylamide, 2-(N,N,N-trimethylammonium) ethyl methacrylate and the like.

The polymers can be applied in the form of an aqueous or non-aqueous solution or emulsion as a coating or finish to modify the free surface energy of a substrate, e.g. a non-porous substrate such as glass, metal, plastic, and ceramic or a fibrous or porous substrate such as textile, e.g., nylon carpet fiber or polyester outerwear fabrics, leather, paper, paperboard, and wood to impart oil and water repellency thereto, as described, for example, in the Banks reference supra.

The relative amounts of various comonomers which can be used with the monomers of this invention generally will be selected empirically and will depend on the substrate to be treated, the properties desired from the fluorochemical treatment, e.g., the degree of oil and/or water repellency desired, and the mode of application to the substrate. Generally, in the case of copolymers, of the interpolymerized or repeating units in the polymer chain, 5 to 95 mole percent of such units will contain pendant perfluoroalkyl groups. The fluoroaliphatic polymers of this invention can be blended with other or known polymers, such as perfluoromethyl-terminated fluoroaliphatic vinyl polymers, and the blend used to modify surface properties, e.g. of textiles such as fabrics to provide them with improved properties such as oil and water repellancy.

Fluorochemicals of this invention which are useful as surfactants generally are those having a polar group such as $-CO_2Na$, $-SO_2NHC_3H_6N^+(CH_3)_3Cl^-$, $-SO_2N(C_2H_5)C_2H_4O(C_2H_4O)_7H$, and $-CONHC3H_6N^+(CH_3)_2CH_2CO_2-$, these moieties being representative of the polar groups in anionic, cationic, non-ionic, and amphoteric surfactants, respectively. The surfactants are useful in improving or imparting properties to aqueous and non-aqueous (organic) liquid systems such as wetting, penetration, spreading, leveling, foaming, foam stabilization, flow properties, emulsification, dispersability, and oil, water, and soil repellency. Said liquid system generally will comprise a liquid phase (in which the surfactant will be dissolved or dispersed) and one or more other phases selected from the group consisting of another liquid phase, a gas phase, and a phase of dispersed solids (e.g. polymer solids), and the system can be in the form of an emulsion, suspension, or foam (such as an air foam). Examples of such liquid systems, or application areas for said surfactants, include rinsing, cleaning, etching, and plating baths, floor polish emulsions, photographic processes, water base coatings, powder coatings, solvent based coatings, alkaline cleaners, fluoropolymer emulsions, soldering systems, and specialty inks, such as described, for example, in 3M Bulletin 98-0211-2213-4 (38.3) BPH.

The fluorochemicals useful as surfactants also can be incorporated into or mixed with other substances. For example, if sufficiently thermally stable, they can be incorporated into polymeric materials, such as polyamides, e.g. nylon, or polyolefins, e.g., polypropylene, which are cast, blown, extruded, or otherwise formed into shaped articles, such as films and fibers, the so-incorporated fluorochemicals modifying the properties of the shaped articles, such as the oil and water repellency of their surfaces. The fluorochemical surfactants of this invention can also be mixed with other surfactants, such as hydrocarbon surfactants and/or the conventional fluorochemical surfactants, e.g. those disclosed in said U.S. Pat. Nos. 2,567,011 and 2,732,398, and such mixed surfactants used to form, for example, aqueous, film-forming foams as described in U.S. Pat. No. 3,562,156 (Francen).

In the following examples, it is shown that the fluorochemical compositions of this invention impart improved properties. As shown in the working examples below, some of the compositions of this invention impart improved oil repellency to textile substrates compared to fluorochemical compositions derived from ECF and containing a sulfonamido linking group. As also shown, some of the compositions of this invention provide lower surface tension to, and have better solubility in, organic or aqueous systems compared to fluorochemical compositions obtained from telomerization (compositions where all compounds have straight-chain, or where all compounds have branched-chain perfluoroalkyl groups).

A convenient route to the perfluoroalkyl halide mixtures of this invention utilizes perfluoroalkyl sulfonyl fluorides (obtained from ECF) according to the following illustrative schemes.

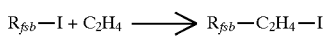

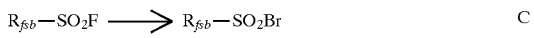

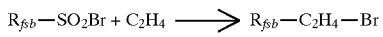

The perfluoroalkyl halide mixtures from Schemes A, B and C are readily converted to various derivatives containing for example hydroxyl, thiol, amino, acids, acid salts, esters, etc., and adducts and derivatives thereof, e.g., urethanes, acrylates and polymers thereof, etc., using conventional synthetic procedures, many of which are described in the examples. Each perfluoroalkyl halide mixture can be converted to either of the other two perfluoroalkyl halide mixtures.

In the following examples, all of the perfluoroalkyl sulfonyl fluorides utilized in Examples of this invention were prepared from the hydrocarbon precursors by electrochemical fluorination (ECF).

EXAMPLES

The following procedures were used where referred to in the examples.

Padding Application Procedure

Polymer emulsions were applied to a 100% cotton fabric (bleached mercerized cotton poplin, style #407, obtained from Test Fabrics, Inc., Middlesex, N.J.) by immersing the fabric in the treatment bath using a padding technique well known to those skilled in the art. The saturated fabric was run through a roller to remove excess emulsion to give a wet pick-up of approximately 60%. After treatment, the wet cotton fabric was dried and cured by placing in a forced air oven set at 150° C. for 10 minutes to give a percent solids on fabric of approximately 0.3% SOF.

Oil Repellency Test

The oil repellency of the treated fabric was measured using AATCC Test Method 118-1975, "Oil Repellency: Hydrocarbon Resistance Test" as described in *AATCC Technical Manual*, 1977, 53, 223. This test measures the resistance of a fibrous substrate to wetting by a series of hydrocarbon liquids, with a range of surface tensions.

Treated fabrics are given an "Oil Repellency" (OR) value ranging from "0" (least repellent) to "8" (most repellent).

Spray Rating Test

The resistance of the treated fabric to wetting with water, was measured using AATCC Test Method 22-1977, "Water Repellency: Spray Test" as described in *American Association of Textile Chemists and Colorists Technical Manual*, 1977, 53, 245. Treated fabrics are given a "Spray Rating" (SR) value on a scale of "0" to "100", with "0" indicating complete wetting of the upper and lower surfaces of the substrate and with "100" indicating no wetting.

Laundering Procedure

The procedure set forth below was used to prepare treated samples designated in the examples below as "5× Laundered".

A 230 g sample of generally square, 400 cm$^2$ to about 900 cm$^2$ sheets of treated substrate is placed in a conventional washing machine along with a ballast sample (1.9 kg of 8 oz fabric in the form of generally square, hemmed, 8100 cm$^2$ sheets). Conventional detergent (TIDE™, 46 g, available from Procter & Gamble Co., Cincinnati, Ohio) is added and the washer is filled to high water level with hot water (40° C.±3° C). The substrate and ballast load is washed five times using a 12-minute normal wash cycle and the substrate and ballast are dried together in a conventional clothes dryer set on the "heat" setting for about 45 minutes. The dry substrate is pressed using a hand iron set at the temperature recommended for the particular substrate fabric.

Dry Cleaning Procedure

Substrate samples designated in the examples below as "Dry Cleaned" were treated as set forth in AATCC Test Method 7-1975, note 8.1. One dry cleaning cycle was used in all cases.

Example 1

In this example, the conversion of a perfluoroalkyl sulfonyl fluoride to a 1,1,2,2-tetrahydroperfluoroalkyl iodide, $R_{fsb}CH_2CH_2I$, will be described. Into a three-necked 5 L flask, fitted with a reflux condenser, thermometer, and stirrer, were placed 585 g 1,4-dioxane, 585 g deionized water and 248 g sodium sulfite. Using the synthetic procedure outlined in U.S. Pat. No. 3,420,877, Example 2, except 700 g perfluorodecanesulfonyl fluoride was used instead of perfluorooctanesulfonyl fluoride, and 435 g iodine instead of bromine. The perfluorodecanesulfonyl fluoride used comprised a mixture of about 65% straight-chain isomer and about 35% branched-chain isomer. After the reaction was completed, the perfluorodecyliodide formed was steam distilled out of the reaction mixture to give 428 g (72%) yellow product boiling 94° C. to 100° C. The product was washed at about 45° C. with a 400 g 10% sodium sulfite solution in water. The product (419 g) was a colorless liquid at 45° C. and a solid-liquid mixture at room temperature. F-NMR analysis indicated that about 65% of the perfluoroalkyl chains were linear, about 10% contained a perfluorinated isopropyl branch, —CF(CF$_3$)$_2$ at the end of the carbon chain, about 0.2% contained a terminal perfluoro t-butyl group —C(CF$_3$)$_3$ and the remainder contained internal branches. The F-NMR data were obtained by using a solution of the product in acetone D6 and using a 94.2 MHz F-NMR instrument.

Into a 3 L steel kettle were placed 295 g (0.45 mole) of perfluorodecyl iodide from above, 1.8 g di t-butylperoxide and 4.6 g catalyst. The catalyst was prepared by mixing 30 g alumina, 2 g anhydrous cupric chloride, 2 g tin tetrachloride and 8 mL 2-aminoethanol. The reactants formed a blue-violet powder. The reactor was degassed and a nitrogen atmosphere was established. 12.8 g ethylene (0.45 mole) was charged into the reactor in 3 equal portions. After each addition, the pressure rose to about 120 psi (0.83 MPa) at a temperature of 108° C. In about 30 minutes after the first addition, the pressure dropped to about 40 psi (0.28 MPa) and the second portion of ethylene was added. The third portion was added in similar fashion. After all the ethylene was charged, the heating was continued at 108° C. until the pressure had decreased to 40 psi (0.28 MPa) and stabilized at this pressure, indicating all ethylene was consumed. The warm reaction product was drained from the reactor. A slightly yellow solid product (307 g) was obtained. H-NMR analysis indicated that the perfluorodecyl tetrahydroiodide $C_{10}F_{21}CH_2CH_2I$ was formed. The product was dissolved in 1000 g acetone, and the catalyst filtered off. After solvent evaporation, a slightly yellow solid was obtained. F-NMR analysis indicated that the perfluorinated chain composition of the perfluorodecyl tetrahydroiodide product was essentially the same as that of the perfluoroecyliodide precursor.

Examples 2–5

Following the procedure outlined in Example 1, the products of Examples 2 to 5 were prepared.

TABLE 1

| Ex. | Starting Material (% straight-chain isomer) | End Product |
|---|---|---|
| 2 | $C_4F_9SO_2F$ (90%) | $C_4F_9CH_2CH_2I$ |
| 3 | $C_6F_{13}SO_2F$ (80%) | $C_6F_{13}CH_2CH_2I$ |
| 4 | $C_8F_{13}SO_2F$ (70%) | $C_8F_{17}CH_2CH_2I$ |
| 5 | *$C_{10}F_{21}SO_2F$ (about 40%) | $C_{10}F_{21}CH_2CH_2I$ |

*Perfluorodecanesulfonyl fluoride at room temperature was a mixture of liquid components and semi-solid components. In Example 1, the semi-solid $C_{10}F_{21}SO_2F$ was used; F-NMR indicated that this fraction contains a major portion (about 65%) of linear perfluorinated chains. In Example 5, the liquid components of perfluorodecanesulfonyl fluoride (about 40% linear, 60% branched) were used. F-NMR indicated the following composition of the resulting perfluordecyltetrahydroiodide product of Example 5: about 40% linear perfluorinated chain, about 10% terminal perfluoroisopropyl group, about 3.0% terminal perfluoro t-butyl group and the remainder (about 44.5%) internally branched material, $CF_3$—$(CF_2)_x$—$CF(CF_3)$—$(CF_2)_y$—, where x and y are each greater than zero.

F-NMR indicated that the products of Examples 2–4 comprised a mixture of compounds with the following approximate composition: linear chains, $CF_3$—$(CF_2)_x$—, 70–90%; branched-chains 10–30% comprising perfluoroisopropyl branches, $(CF_3)_2CF(CF_2)_x$, about 10%; perfluoro t-butyl branches, $(CF3)_3C$—$(CF_2)_x$ about 0.3%; and internal branching, about 15 to 20%.

In Examples 6–11, the conversion of perfluoroalkanesulfonyl fluorides to tetrahydrochlorides (Examples 6–10) and homologs and a tetrahydrobromide (Example 11) are described.

Example 6

Perfluorooctanesulfonyl chloride was prepared from the corresponding sulfonyl fluoride (U.S. Pat. No. 3,420,877) containing about 70% straight-chain and 30% branched-chain isomers. The crude reaction product was washed with water, dilute aqueous potassium bicarbonate, water and dried with anhydrous sodium sulfate. Perfluorooctanesulfonyl chloride (12 g, 0.0232 mole) and di t-butyl peroxide (0.40 g) were added to a thick wall glass ampoule. The ampoule was placed in a liquid nitrogen bath, evacuated with a pump, then ethylene (1.28 g, 0.046 mole) was condensed into the ampoule. The ampoule was sealed, placed into a Hastalloy B vessel which had been padded with a glass wool cushion, and the vessel was pressurized with nitrogen gas (to balance the pressure inside the ampoule). The reaction vessel was heated at 115° C. for 6 hours, cooled to room temperature; then the glass ampoule cooled in liquid nitrogen and opened to yield a dark brown, semi-solid product (11 g). GC/MS analysis showed the product to be a mixture of $C_8F_{17}CH_2CH_2Cl$ and $C_8F_{17}(CH_2CH_2)_2Cl$. NMR analysis showed a product ratio of 2:1 of the 1 to 1 and 1 to 2 adducts. The product contained a mixture of compounds, 70% of which contained straight-chain and 30% of which contained branched-chain perfluoroalkyl group.

Example 7

In this example, in order to better control the product ratios, ethylene was added incrementally to a heated mixture of perfluorooctanesulfonyl chloride using di t-butyl peroxide as free radical initiator. Thus a mixture of $C_8F_{17}SO_2Cl$ (300 g, 0.58 mole) and di t-butyl peroxide initiator (1.8 g) was charged into a 300 mL Monel reactor. Ethylene (2.6 g) was added, and the mixture was heated with shaking to 115° C. Additional ethylene charges (2.5, 4.0, 3.0, and 2.7 g) were incrementally added over a three hour period for a total of 14.7 g of ethylene. Upon cooling to room temperature a slushy product (303 g), mainly $C_8F_{17}C_2H_4Cl$ was obtained.

Example 8

Similarly, $C_8F_{17}SO_2Cl$ (30 g) was dissolved in isooctane (30 g), benzoyl peroxide (0.1 g) added and the mixture agitated at 100° C. in a glass lined Hastalloy B reactor containing excess ethylene gas (8 g). After an eight hour reaction time at 100°–105° C., the product, mainly $C_8F_{17}C_2H_4Cl$, was isolated as a light, cream-colored solid.

Example 9

A mixture of 10 g (0.024 mole) perfluorohexanesulfonyl chloride containing about 80% straight-chain isomer, ethylene (1.3 g, 0.046 moles), and di t-butyl peroxide (0.4 g) was placed in a glass ampoule. The mixture was heated at 100° C. for 18 hours. The product was isolated as a dark-colored liquid. GC analysis showed a product ratio of 3:2 of 1:1 and 1:2 adducts. Mass spectral analysis and plasma chromatography showed the products contained no sulfur and had the structures $C_6F_{13}CH_2CH_2Cl$ and $C_6F_{13}(CH_2CH_2)_2Cl$.

Example 10

Perfluorodecanesulfonyl chloride prepared from the corresponding sulfonyl fluoride (about 60% straight-chain isomer), was used to prepare the corresponding tetrahydrochloride product. The perfluorodecanesulfonyl chloride (20.0 g, 0.032 mole), ethylene (5.0 g, 0.17 mole) and azobisisobutyronitrile (VAZO 64) were placed in a glass-lined 180 mL capacity Hastalloy B reactor and the vessel shaken and heated to 70°–75° C. for 16 hours. The reaction vessel was cooled, excess pressure released, and the product (21.3 g) isolated as a waxy solid. A sample was purified by vacuum sublimation to afford a white crystalline product. Analysis by NMR and GC/MS verified the product to be a mixture of predominantly 1:1 and 1:2 adducts having the structure $C_{10}F_{21}(CH_2CH_2)_nCl$ where n is mainly 1 and 2 with a very small amount of (<5%) product where n=3.

Example 11

Perfluorobutanesulfonyl bromide was prepared using the method described by Harzdorf in Justus Liebig's Annalen der Chemie 1973, 33–39, whereby perfluorobutane sulfinic acid (from $C_4F_9SO_2F$ about 90% linear isomer) was brominated in acetic acid. A mixture of perfluorobutanesulfonyl bromide (10.0 g, 0.0226 moles), ethylene (0.046 moles) and di t-butyl peroxide 10.4 g) was heated at 90° C. for 16 hours in a glass-lined 180 cc Hastalloy B reactor. At the end of the reaction, a dark liquid (6.5 g) was isolated. The acidic components in the reaction mixture were removed by washing the liquid phase with aqueous potassium bicarbonate solution followed by two water washes and drying with sodium sulfate. GC/MS analysis showed the presence of a low boiling component ($C_4F_9Br$) and the desired products $C_4F_9CH_2CH_2Br$ and $C_4F_9(CH_2CH_2)_2Br$ in a 2:3 ratio.

Example 12

In this example, the conversion of a perfluoroalkyltetrahydroiodide to a perfluoroalkyl tetrahydroalcohol will be described.

Into a 3 L, three-necked flask, fitted with a stirrer, a reflux condenser, and a thermometer, were placed 574 g (1 mole) of $C_8F_{17}CH_2CH_2I$, as prepared in Example 4, 594 g (6 moles) of N-methylpyrrolidone and 72 g (4 moles) of water. The mixture was heated to reflux (about 117° C.). The reaction was continued for 40 hours to yield a dark brown reaction mixture, which was cooled to about 80° C. to give a 2 phase reaction mixture. Deionized water (1 L) was added and the mixture heated to 70° C. for 1 hour to give 2 liquid phases. The brown bottom phase containing the reaction product was separated and washed two additional times at about 70° C. using 1 L of water each time. The bottom product phase was separated from the water layer and purified by steam distillation using a Dean Stark trap with 400 mL water. Product boiling from 94° C. to 102° C. was collected. Total yield was 475 g, about 40 g was liquid, the remaining 435 g a slushy solid. The liquid was identified by H-NMR and GC-MS to be the olefin, $C_8F_{17}CH=CH_2$. The solid analyzed by gas chromatography was shown to be the 95% of the tetrahydroalcohol, $C_8F_{17}CH_2CH_2OH$. The remainder was unreacted tetrahydroiodide. The yield of tetrahydroalcohol was 84%. F-NMR analysis indicated that the product mixture, contained about 74% linear chains, about 11% terminal perfluoroisopropyl groups, about 0.2% terminal perfluoro t-butyl groups, and about 14% internal branching. Upon standing at room temperature, the slushy solid separated into 2 physical phases: a small top liquid phase and a major bottom semi-solid phase. The top liquid was separated off and analyzed by F-NMR. The mixture of compounds of the liquid phase contained about 44% linear materials, about 12% terminal perfluoroisopropyl groups, about 0.3% terminal t-butyl groups, and about 43% internal branches.

Examples 13, 14

Using the procedure outlined in Example 12, the following perfluoroalkyl tetrahydroalcohols were made from the tetrahydroiodides of Examples 1 and 2.

TABLE 2

| Ex. | STARTING MATERIAL (% straight-chain) | END PRODUCT | YIELD |
|---|---|---|---|
| 13 | $C_4F_9CH_2CH_2I$ (90%) | $C_4F_9CH_2CH_2OH$ | 88% |
| 14 | $C_{10}F_{21}CH_2CH_2I$ (65%) | $C_{10}F_{21}CH_2CH_2OH$ | 80% |

Example 15

In this example, the conversion of perfluoroalkyl tetrahydroiodide to a perfluoroalkyl tetrahydrothiol will be described.

Into a 3 L, three-necked flask, fitted with a stirrer, a thermometer, and a reflux condenser, were placed 574 g (1 mole) of perfluorooctyl tetrahydroiodide (prepared as described in Example 4), $C_8F_{17}CH_2CH_2I$, 114 g (1.5 mole) of thiourea and 400 g of ethanol. The reaction mixture was heated at 75° C. under a nitrogen atmosphere for 5 hours. The reaction was cooled to 50° C. under nitrogen. Then 120 g of a 50% solution of NAOH (1.5 mole) and 200 g deionized water were added and heating at 50° C. continued for 1 hour. Addition of 1 L of water gave 2 liquid phases. The brown bottom phase containing the reaction product was washed twice with 1 L of water at room temperature and the product phase separated. A Dean Stark trap was set up, 400 g of water added, and the perfluoroalkyl tetrahydrothiol product steam distilled at a temperature of 94° C. to 99° C., to give 430 g of a colorless liquid product. Gas chromatographic analysis indicated an 84% yield of $C_8F_{17}CH_2CH_2SH$, and about 2% olefin, $C_8F_{17}CH=CH_2$. F-NMR indicated that the $C_8F_{17}CH_2CH_2SH$ product mixture contained about 77% linear chains, about 9% terminal perfluoroisopropyl groups, about 0.2% terminal perfluoro t-butyl groups, and about 13% internal branching.

Examples 16–19

Using the procedure outlined in Example 15, the following perfluoroalkyl tetrahydrothiols were made:

TABLE 3

| Ex. | STARTING MATERIAL (% straight-chain) | END PRODUCT | YIELD |
|---|---|---|---|
| 16 | $C_4F_9CH_2CH_2I$ (90%) | $C_4F_9CH_2CH_2SH$ | 75% |
| 17 | $C_{10}F_{21}CH_2CH_2I$ (65%) | $C_{10}F_{21}CH_2CH_2SH$ | 88% |
| 18 | $C_{10}F_{21}CH_2CH_2I$ (40%) | $C_{10}F_{21}CH_2CH_2SH$ | 85% |
| 19 | $C_8F_{17}(CH_2CH_2)_{1.3}Cl$ (70%) | $C_8F_{17}(CH_2CH_2)_{1.3}SH$ | 33% |

Example 20

In this example, the conversion of a perfluoroalkyl tetrahydroalcohol into the corresponding perfluoroalkyl acrylate is described.

Into a three-necked 500 mL flask, fitted with a condenser, a stirrer, and a thermometer, were placed 232 g (0.5 mole) of perfluorooctyl tetrahydroalcohol (prepared as described in Example 12) $C_8F_{17}CH_2CH_2OH$, and 90 g methyl ethyl ketone (MEK). Using a Dean Stark trap, 20 g MEK was distilled out, the reaction mixture cooled to room temperature under nitrogen, then 50.5 g (0.5 mole) of dry triethylamine and 100 ppm Irgonox 1010 antioxidant (Ciba-Geigy) were added. Using an addition funnel and a nitrogen purge, 45 g (0.5 mole) of acryloyl chloride were added over a 1 hour period. An exotherm of about 20° C. was noticed. A white slurry was obtained in the exothermic (about 20° C. temperature rise) reaction. After the addition was complete, the reaction mixture was maintained at 50° C. for 2 hours. Gas chromatographic analysis indicated a conversion of 95% to acrylate. The reaction mixture was washed three times using 200 mL of water. The yield of colorless liquid product, $C_8F_{17}CH_2CH_2OCOCH=CH_2$, was 237 g (94%).

Example 21

Following the procedure of Example 20, $C_4F_9CH_2CH_2OCOCH=CH_2$, was prepared in a 90% yield as a slightly yellow liquid, starting from the alcohol of Example 13.

Comparative Example 22

In this example, the conversion of perfluoroalkyl tetrahydroiodide into a perfluoroalkyl olefin will be described.

Into a 1 L, three-necked flask, fitted with a condenser, a thermometer, and a stirrer, were placed 57.5 g (0.1 mole) perfluorooctyl tetrahydroiodide as prepared in Example 4, 100 g isopropanol and 8.4 g (0.15 mole) potassium hydroxide. The reaction mixture was heated at reflux for 5 hours to give a brown reaction mixture. Gas chromatographic analysis showed a conversion to about 96% olefin. Deionized water (400 mL) was added and the reaction mixture was steam distilled using a Dean Stark trap. In a temperature range 94°–98° C., 43 g (95%) of colorless liquid olefin product, $C_8F_{17}CH=CH_2$, was obtained in a purity greater than 98%. F-NMR analysis indicated that the mixture of compounds contained about 74% linear material, about 10% terminal perfluoroisopropyl, about 0.2% terminal perfluoro t-butyl, and about 13% internal branching.

Example 23

Following the procedure of Example 22, $C_{10}F_{21}CH=CH_2$ was prepared from the tetrahydroiodide of Example 5. This olefin product mixture contained about 42% linear perfluorinated chains, about 10% perfluoroisopropyl terminated, and about 46% internally branched material.

Example 24

In this example, the conversion of a perfluoroalkyl tetrahydroalcohol into a perfluoroalkyl dihydrocarboxylic acid is described.

Into a 1 L, three-necked flask, fitted with a reflux condenser, a thermometer, and a stirrer, were placed 46.6 g (0.1 mole) of tetrahydroalcohol, $C_8F_{17}CH_2CH_2OH$ (prepared in Example 6), and 450 g acetone. The solution was cooled to about 5° C. in an ice bath and 23.7 g (0.15 mole) of potassium permanganate added in small portions over a 2 hour period. The reaction was exothermic, and a color change from purple to brown was observed. After all the potassium permanganate had been added, the reaction was allowed to react for 1 hour at room temperature. The reaction was then slowly heated up to reflux temperature (about 58° C.) and maintained for about 3 hours. Then 50 g of water were added to the brown product slurry and all acetone was removed by distillation. The reaction was cooled to about 5° C. using an ice bath, and 100 g of 95% sulfuric acid were added slowly over a 2 hour period. After the acid addition, the reaction mixture was heated at 95° C. for 2 hours. After cooling to about 40° C., 200 mL of water was added to the two-phase mixture. The brown bottom phase was separated from the water layer at 65° C. and washed twice using 200 mL water at 75° C. The bottom phase was collected and distilled. The product fraction collected from 100° C. to 130° C. at about 20 torr yielded 35 g of a solid material at room temperature. GC-MS analysis indicated the presence of about 78% $C_8F_{17}CH_2COOH$, about 11% $C_8F_{17}CH_2COOCH_2CH_2C_8F_{17}$ (ester of the starting alcohol and the formed acid) and about 10% $C_8F_{17}COOH$. The yield of perfluorooctyl dihydrocarboxylic acid, $C_8F_{17}CH_2COOH$, was about 57%.

Example 25

Into a 500 mL three-necked flask, fitted with a reflux condenser, a thermometer, and a stirrer, were placed 61.8 g (1 mole) boric acid, 232 g (4 moles) allyl alcohol and 120 g toluene. A Dean Stark trap was used to collect water during the azeotropic distillation. The initial white slurry present before the reaction mixture was heated became a clear solution after heating to reflux and forming 53 g of water in the azeotropic distillation. Toluene, excess allyl alcohol and triallyl borate ester product were distilled off. The triallyl borate (161 g, 89%) was obtained as a colorless, viscous liquid. Into a 500 mL three-necked flask, fitted with a reflux condenser, a thermometer, and a stirrer were placed 18.2 g (0.1 mole) of the above triallyl borate, 20 g ethyl acetate, 103.8 g (0.3 mole) $C_4F_9I$, prepared following Example 1a, and 0.2 g azobisisobutyronitrile (AIBN). The mixture was heated at about 40° C. and degassed using aspirator vacuum and nitrogen. The reaction mixture was heated to reflux, and an additional 0.2 g of AIBN were added. Heating at reflux was continued for 15 hours under a nitrogen atmosphere, followed by addition of another 0.2 g of AIBN and refluxing for an additional 5 hours. Gas chromatographic analysis of the clear, yellow product solution indicated that about 2% of unreacted $C_4F_9I$ was left unreacted and that the major product was $C_4F_9CH_2CH(I)CH_2OH$. After addition of 230 g of deionized water and distilling off ethyl acetate, the reaction mixture was heated at 95° C. for 1 hour. The bottom yellow-brown organic layer containing the reaction product was washed twice with 200 g of water at 95° C.

Example 26

To the yellow-brown liquid product from Example 25 was added at room temperature, 24 g (0.3 mole) of a 50% aqueous sodium hydroxide solution, 100 g isopropanol and 30 g water. The reaction mixture was heated at 40° C. for 2 hours, then 300 g of water were added. The brown bottom phase of the mixture, containing the reaction product, was washed twice with 200 g water. Distillation at reduced pressure gave 61.7 g (74% yield) of epoxy

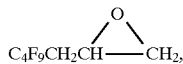

in a purity of 93% as determined by GC, and H- and F-NMR analysis. A by product (3%) was $C_4F_9CH=CHCH_2OH$. The epoxy product mixture contained about 74% straight-chains, about 11% terminal perfluoroisopropyl branches and about 14% internal branching.

Example 27

Following the same procedure as in Examples 25 and 26,

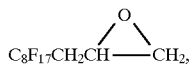

was prepared from $C_8F_{17}I$ and triallyl borate. The intermediate product $C_8F_{17}CH_2CH(I)CH_2OH$ was not isolated.

The following Table shows the structures of the major products in the mixtures produced in Examples 1/27. Table 4 also lists the weight % of compounds containing a straight-chain perfluoroalkyl group and the weight % of compounds containing a branched-chain perfluoroalkyl group in each product mixture.

TABLE 4

| | Percent straight and branched Perfluoroalkyl Groups | | |
|---|---|---|---|
| Examples | Product | straight | branched |
| 1 | $C_{10}F_{21}CH_2CH_2I$ | 65 | 35 |
| 2 | $C_4F_9CH_2CH_2I$ | 90 | 10 |

TABLE 4-continued

| | Percent straight and branched Perfluoroalkyl Groups | | |
|---|---|---|---|
| Examples | Product | straight | branched |
| 3 | $C_6F_{13}CH_2CH_2I$ | 83 | 17 |
| 4 | $C_8F_{17}CH_2CH_2I$ | 74 | 26 |
| 5 | $C_{10}F_{21}CH_2CH_2I$ | 40 | 60 |
| 6 | $C_8F_{17}(CH_2CH_2)_{1.3}Cl$ | 70 | 30 |
| 7 | $C_8F_{17}(CH_2CH_2)_1Cl$ | 70 | 30 |
| 8 | $C_8F_{17}(CH_2CH_2)_1Cl$ | 70 | 30 |
| 9 | $C_6F_{13}(CH_2CH_2)_{1.4}Cl$ | 80 | 20 |
| 10 | $C_{10}F_{21}(CH_2CH_2)_{1.3}Cl$ | 60 | 40 |
| 11 | $C_4H_9(CH_2CH_2)_{1.6}Br$ | 90 | 10 |
| 12 | $C_8F_{17}CH_2CH_2OH$* | 74 | 26 |
| | $C_8F_{17}CH_2CH_2OH$** | 44 | 56 |
| 13 | $C_4F_9CH_2CH_2OH$ | 91 | 9 |
| 14 | $C_{10}F_{21}CH_2CH_2OH$ | 63 | 37 |
| 15 | $C_8F_{17}CH_2CH_2SH$ | 77 | 23 |
| 16 | $C_4F_9CH_2CH_2SH$ | 89 | 11 |
| 17 | $C_{10}F_{21}CH_2CH_2SH$ | 65 | 35 |
| 18 | $C_{10}F_{21}CH_2CH_2SH$ | 40 | 60 |
| 19 | $C_8F_{17}(CH_2CH_2)_{1.3}SH$ | 75 | 25 |
| 20 | $C_8F_{17}CH_2CH_2OCOCH=CH_2$ | 77 | 23 |
| 21 | $C_4F_9CH_2CH_2OCOCH=CH_2$ | 90 | 10 |
| 22 | $C_8F_{17}CH=CH_2$ | 74 | 26 |
| 23 | $C_{10}F_{21}CH=CH_2$ | 42 | 58 |
| 24 | $C_8F_{17}CH_2COOH$ | 75 | 25 |
| 25 | $C_4F_9CH_2CH(CH_2OH)I$ | 90 | 10 |
| 26 | $C_4F_9CH_2CH{-}CH_2$ (epoxide) | 89 | 11 |
| 27 | $C_8F_{17}CH_2CH{-}CH_2$ (epoxide) | 74 | 26 |

*Slushy Product
**Liquid Phase

Example 28

In this example, the conversion of a perfluoroalkyl tetrahydrothiol to a perfluoroalkyl melamine is described.

Into a 500 mL three-necked flask, fitted with a stirrer, a reflux condenser, and a thermometer, were placed 39.0 g (0.1 mole) hexametboxymethyl melamine (HMMM) available from American Cyanamid, as Aerotex 302), 192 g (0.4 mole) perfluorooctyl tetrahydrothiol, from Example 15 and 0.34 g p-toluene sulfonic acid. The action mixture was slowly heated to 80° C. under nitrogen. Methanol forming in the reaction caused some foaming. The temperature was slowly increased over a 2 hour period to 120° C. In this period, about 10 g of methanol was formed and trapped in a Dean Stark trap. The foam had completely collapsed. The reaction mixture was heated during 30 minutes from 120° C. to 180° C. under nitrogen yielding an additional 2.5 g methanol in the Dean Stark trap. Heating of the reaction mixture was continued at 180° C. for 5 hours under a nitrogen atmosphere. The condensation reaction product was a yellow-brown solid at room temperature and comprises a mixture of compounds of formula $C_3N_6(CH_2OCH_3)_x(CH_2SC_2H_4C_8F_{17})_y$, where x and y have average values of about 2 and 4, respectively.

Into a 500 mL three-necked flask, fitted with a reflux condenser, a thermometer, and a stirrer, were charged 180 g solids of the above prepared condensate (from (a)) and 270 g butyl acetate. The reaction mixture was heated at 65° C. to yield a clear yellow-brown solution.

Into a separate 1 L beaker were placed 18.0 g Marlowet™ 5401 emulsifier (Huls, Germany), 108 g ethyl Cellosolve™ and 720 g of deionized water and stirred and heated to about 65° C. until a clear solution resulted. While stirring vigorously, the above butyl acetate solution of the fluorochemical melamine product was added to the aqueous solution at about 65° C. A preemulsion resulted, which was passed through a preheated (at 70° C.) Manton-Gaulin emulsifier at about 4000 psi (27.6 MPa) pressure. A yellow-brown, nearly transparent emulsion at about 70° C. resulted. The solvent was removed using a vacuum pump at about 1 to 10 torr and 50° C. A nearly transparent, aqueous dispersion resulted. The solids content was about 18%.

Example 29, Comparative Examples C1–C3

Following the same procedure as in Example 28, Example 29 and Comparative Examples C1–C3 were prepared, as shown below. The Comparative Examples $C_2$ and C3 contain straight-chain fluoroalkyl groups only. Comparative Example C1 contains a sulfonamido group directly attached to the perfluoroalkyl group.

TABLE 5

| EX. | FLUOROCHEMICAL INTERMEDIATE USED | MOLAR RATIO HMMM/FC-INTERMEDIATE |
|---|---|---|
| 29 | $C_{10}F_{21}CH_2CH_2SH$ as prepared in Example 18 | 1:4 |
| C1 | $C_8F_{17}SO_2N(CH_3)CH_2CH_2OH$ (available from 3M) | 1:4 |
| C2 | $C_nF_{2n+1}CH_2CH_2SH$ with <n> = 10 (available from Ciba Geigy) | 1:4 |
| C3 | $C_nF_{2n+1}CH_2CH_2OH$ with <n> = 8 (available from DuPont) | 1:4 |

Examples 28 and 29, and Comparative Examples C1–C3 (containing $R_{fs}$ groups), were used as dispersions to treat textile fabrics.

An aqueous treatment bath, which is usually a dispersion or emulsion, is prepared containing the fluorochemical compositions and other required or desired ingredients such as resins, catalysts, extenders, softeners, etc. The textile fabric is immersed in the treatment bath by a padding technique, which is well known to those skilled in the art. The saturated fabric is run through a roller to remove excess dispersion/emulsion, dried and cured in an oven for the desired temperature and time. The resulting treated fabrics are tested for oil and water repellency by test methods set forth below:

| Water spray (SR) test | AATCC Test Method 22-1977 |
|---|---|
| Oil repellency (OR) test | AATCC Test Method 118-1975 |
| Bundesmann test: | Deutche Industries Norm (DIN) 53-888 |
| Dry cleaning procedure: | AATCC Test Method 7-1975 |
| Laundering procedure: | A 230 g sample of 400 cm² to about 900 cm² of treated fabric is placed in a conventional washing machine along with a ballast sample (1.9 kg of 8 oz. fabric). Conventional detergent (46 g) is added and the washer filled to high water level with hot water (40 ± 3° C.). The substrate and ballast is washed 5 times using 12 minute normal wash cycle and the substrate and ballast are dried together in a conventional clothes dryer for about 45 minutes. The dry substrate is pressed using a hand iron set at the temperature recommended for the particular fabric. |

Evaluation (using the above test methods and procedures) of fabric samples treated with the compositions of Examples 28 and 29 and Comparative Examples C1, C2, and C3 is given in Table V below.

A polyester/cotton 50/50 blend fabric was treated at 0.3% solids by weight on total weight of the fabric using a treatment bath containing: a) the fluorochemical melamine dispersions containing approximately 18 wt. % solids, as described above; b) 12 g/L resin LYOFIX CHN (Chem. Fabrik Pfersee, Germany) 6 g/L Knittex catalyst 20 (Chem. Fabrik Pfersee) and 2 mL/L acetic acid (60%). The treated fabrics were dried and cured at 150° C. for 5 minutes. Results are shown in Table 6.

TABLE 6

| | Initial | | Bundesman | | | After 5 Launderings | | After 1 Dry Cleaning | |
|---|---|---|---|---|---|---|---|---|---|
| | | | 1 | 5 | 10 | | | | |
| Ex. | OR | SR | (Minutes) | | | OR | SR | OR | SR |
| 28 | 6 | 100 | 5 | 5 | 5 | 5 | 90 | 5 | 100 |
| 29 | 5 | 100 | 5 | 5 | 5 | 4 | 80 | 5 | 90 |
| C1 | 3 | 100 | 4.5 | 4.5 | 4 | 2 | 90 | 2 | 100 |
| C2* | 5 | 100 | 5 | 5 | 5 | 3 | 90 | 4 | 100 |
| C3 | 5 | 100 | 4.5 | 3.5 | 3 | 4 | 80 | 4 | 90 |

*In the emulsification step, hexafluoroxylene was used as the organic solvent.

As the results indicate (compare, for example the results for Example 28 to the results for Comparative Examples C1 and C3) the compositions of the invention impart better oil and water repellency to fabrics, and the treated fabrics retain repellency after laundering and dry cleaning. The results show that the compositions obtained from reactions using intermediates of the invention are, at equal carbon atom content in the perfluoroalkyl group, superior to compositions made using intermediates containing 100% straight-chain perfluoroalkyl groups ($R_{fs}$), or compositions with a sulfonamido linking group (containing straight and branched-chain perfluoroalkyl groups). These intermediates of this invention are more effective oil and water repellency agents than those derived from the two other classes of intermediates. Even more surprising is the comparison of Example 28 and Comparative Example C2, which shows that the $C_8$ thiol of this invention gives a product with equal or slightly better properties than the composition derived from a straight-chain $C_{10}$ thiol, indicating a better fluorine efficiency.

Another advantage of these intermediates and compositions of this invention is their superior solubility in organic solvents, which is important if the compositions are used as aqueous dispersions. Comparative Example C2 could only be emulsified when hexafluoroxylene was used as a solvent, while the products of Examples 28 and 29 were easily soluble in a variety of organic solvents such as esters or ketones. The solubility of the product of Comparative Example C3 was also poorer than products of Examples 28 and 29, although better than Comparative Example C2 (perhaps due to its shorter average chain length).

Example 30

Into a 500 mL three-necked flask, fitted with a stirrer, a reflux condenser, and a thermometer, were placed 46.4 g (0.1 mole) of $C_8F_{17}CH_2CH_2OH$ (as prepared in Example 12) and 80 g ethyl acetate. A Dean Stark trap was set up and 20 g ethyl acetate was distilled out. The reaction was cooled to about 40° C. under nitrogen; then 40.8 g (0.3 isocyanate equivalent) of PAPI (an oligomeric aromatic isocyanate of chemical structure:

$OCNC_6H_4CH_2[C_6H3(NCO)]_nCH_2C_6H_4NCO$ (average of n=0.7) available from Upjohn Co.) and 3 drops of dibutyltin dilaurate were added. The reaction was heated to reflux (about 78° C.) under nitrogen, and heating continued for 5 hours at reflux. The reaction mixture was cooled to about 45° C. under N2, then 17.4 g (0.2 mole) of 2-butanone oxime (Servo Comp., The Netherlands) added over about 30 minutes resulting in an immediate exotherm of about 10° C. Heating of the reaction mixture was continued for 1 hour at 60° C., after which time no isocyanate absorption by infrared analysis could be detected. A clear, brown solution containing a fluorochemical oligomeric urethane was obtained.

Into a 500 mL three-necked flask, fitted with a stirrer, a thermometer, and a reflux condenser, were placed the above obtained ethyl acetate solution and 80 g of additional ethyl acetate. The mixture was heated to about 60° C. to yield a clear, brown solution. Into a separate 1 L beaker were placed 10.3 g Marlowet™ 5401 emulsifier (commercially available from Hüls), 60 g ethylene glycol and 355 g deionized water. This solution was heated to about 60° C.; then under vigorous stirring, the organic solution was added to the aqueous solution. The resulting preemulsion was passed 3 times through a preheated Manton Gaulin emulsifier at about 55° C. and 4000 psi (27.6 MPa) pressure. The ethyl acetate solvent was distilled out using an aspirator vacuum to yield a pale brown, slightly transparent aqueous dispersion containing about 18 wt. fluorochemical urethane oligomer.

Comparative Examples C4, C5

Using the same synthetic and emulsification procedure as in Example 30, further examples were prepared as shown in Table VI. Comparative Example $C_4$ was made using N-methylperfluorooctanesulfonamido ethanol, $C_8F_{17}SO_2N(CH_3)CH_2CH_2OH$, (available from 3M Company) and Comparative Example C5 was made using perfluorodecyl tetrahydroalcohol, $ClOF_{21}CH_2CH_2OH$ (available from Hoescht Co., Germany), double the amount of solvent had to be used during emulsification.

Using the same fabric, treatment method and test procedures as described above for Examples 28, 29, and Comparative Examples C1–C3, the following test results were obtained:

TABLE 7

| Treatment with Composition of | Initial | | 5 Launderings | | 1 Dry Cleaning | |
|---|---|---|---|---|---|---|
| Example | OR | SR | OR | SR | OR | SR |
| 30 | 4 | 100 | 3 | 80 | 2 | 80 |
| C4 | 2 | 100 | 0 | 70 | 0 | 70 |
| C5 | 3 | 100 | 2 | 80 | 2 | 70 |

The results indicate again that the compositions of this invention are superior to compositions containing 100% straight-chain perfluoroalkyl group. The compositions of this invention are also superior to sulfonamido derived compositions. Again, the intermediates of this invention show better fluorine efficiency, better performance and better solubility.

Example 31

In this example, compositions of the invention were used to make an oligomeric fluorochemical urethane derivative.

Into a 500 mL three-necked flask was placed 51.8 g (0. 1 mole) of the acrylate prepared in Example 20, 2 g (0.025 mole) of 2-mercaptoethanol, 0.4 g AIBN initiator and 40 g ethyl acetate. The mixture was heated to about 40° C. and degassed. The reaction mixture was then heated at reflux (about 78° C.) for 16 hours under nitrogen. A clear, pale yellow solution was obtained, containing a hydroxy functionalized fluorochemical oligomer of average molecular weight about 2,200. Gas chromatography indicated that virtually all reagents had been reacted. The reaction mixture was cooled to about 45° C. under nitrogen and about 60 g ethyl acetate was added. A Dean Stark trap was set up and 20 g ethyl acetate distilled out. The reaction mixture was cooled to about 45° C. under nitrogen; then 10.2 g (0.075 isocyanate equivalents) of PAPI were added together with three drops of dibutyltindilaurate. The reaction mixture was heated at reflux (about 78° C.) under nitrogen for 5 hours, then cooled to about 50° C. under nitrogen. After addition of 4.3 g 2-butanone oxime (0.05 mole), the reaction mixture was heated at 70° C. for 1 hour. A clear, brown solution was obtained, which was free of isocyanate groups (infrared analysis).

The oligomeric fluorochemical urethane product was emulsified and tested according to the procedures described and used for Example 30. Two commercially available fluorochemical agents were also evaluated. The fabric used was 100% cotton. The results are shown in Table 8.

TABLE 8

| Treatment with Composition of | Initial | | 5 Launderings | | 1 Dry Cleaning | |
|---|---|---|---|---|---|---|
| Example | OR | SR | OR | SR | OR | SR |
| 31 | 6 | 100 | 5 | 90 | 5 | 100 |
| AG-310* | 2 | 100 | 1 | 60 | 2 | 70 |
| Oleophobol PF** | 5 | 100 | 2 | 90 | 3 | 100 |

*AG-310 is a fluorochemical containing commercial product available from Asahi Glass Co., Ltd.
**Oleophobol PF is a fluorochemical containing product available from Chemische Fabrik Pfersee.

As can be seen, Examples of the invention give excellent results, compared to commercially available products, even on fabrics which are known to those skilled in the art to be difficult to treat.

Example 32

In this example, a fluorochemical thiol of the invention was added across the triple bond of propargyl alcohol and the resulting adduct converted into a blocked oligomeric urethane derivative. Into a 500 mL three-necked flask, fitted with a reflux condenser, a thermometer, and a stirrer, were placed 48 g (0.1 mole) of $C_8F_{17}CH_2CH_2SH$ as prepared in Example 15, 2.8 g (0.05 mole) of propargyl alcohol, 20 g methyl ethyl ketone and 0.15 g AIBN. The reaction mixture was degassed and heated at reflux (about 76° C.) under nitrogen. After 6 hours, another 0.15 g AIBN was added, and the reaction continued for 15 hours at reflux under nitrogen to yield a clear, yellow solution. Gas chromatography indicated about 10% residual fluorochemical thiol. The reaction mixture was cooled to about 40° C. under nitrogen; then 40 g methyl ethyl ketone, 20.4 g (0.15 isocyanate equivalents) of PAPI and three drops of dibutyltindilaurate were added. The reaction mixture was heated at reflux under nitrogen for 5 hours. The reaction mixture was cooled again to about 50° C. under nitrogen; then 8.2 (0.01 mole) of 2-butanone oxime was added, and the reaction mixture heated at 70° C. for 1 hour to yield a clear brown solution containing an oligomeric urethane derivative having blocked isocyanate groups and one hydroxy functionalized adduct of the fluorochemical thiols of this invention. The reactions are shown in the following scheme: (See U.S. Pat. No. 4,158,672, Ex. 1)

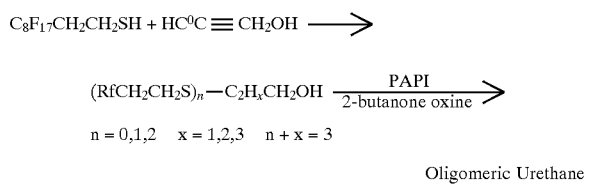

$n = 0,1,2 \quad x = 1,2,3 \quad n + x = 3$

Oligomeric Urethane

The product was emulsified following the procedure outlined in Example 30. Further compositions (Examples 33 and 34) using this procedure and emulsification procedure were prepared and are shown in Table 9.

TABLE 9

| EX. | FC INTERMEDIATE A | FUNCTIONAL ALKYNE B | ISOCYANATE C | EQUIVALENTS RATIO A/B/C/2-BUTANONE OXIME |
|---|---|---|---|---|
| 33 | Example 15 | 2,4-hexadiyne 1,6-diol | TDI* | 4/1/2/1 |
| 34 | Example 15 | 2,4-hexadiyne-1,ol | PAPI | 4/1/3/2 |

*Toluene Diisocyanate

The fluorochemical oligomeric urethane materials of Examples 33 and 34 were used to treat a polyester/cotton 65/35 blend fabric at 0.3% by weight of fluorochemical on fabric by the methods described above. Test results are shown in Table 10.

TABLE 10

| Treatment with Composition of | Initial | | 5 Launderings | | 1 Dry Cleaning | |
|---|---|---|---|---|---|---|
| Example | OR | SR | OR | SR | OR | SR |
| 32 | 6 | 100 | 4 | 90 | 4 | 90 |
| 33 | 3 | 90 | 1 | 50 | 2 | 70 |
| 34 | 7 | 100 | 6 | 80 | 5 | 80 |

As can be seen from the data, excellent results were obtained using the fluorochemical compositions of this invention.

Example 35

Into a carefully dried 500 mL three-necked flask, fitted with a condenser, stirrer, and thermometer, were placed 15.3 g (0.1 mole) of POCl13 (under nitrogen) and 20 g toluene. Deionized water (1.8 g, 0.1 mole) was added dropwise under vigorous stirring over about 15 minutes. An exotherm of about 25° C. was observed and HCl was liberated. The reaction was heated to 70° C. until no more HCl was liberated. Then 46.4 g (0.1 mole) of $C_8F_{17}CH_2CH_2OH$, as prepared in Example 12, was added over 15 minutes. The reaction mixture was heated at 90° C. under a gentle nitrogen flow until no more HCl was liberated (about 3 hours). The reaction was cooled to 50° C. under nitrogen; then 1.8 g (0.1 mole) of deionized water was added. The reaction mixture was heated to 90° C. under a gentle $N_2$ flow until no more HCl was liberated (about 2 hours). Then a gentle vacuum (by aspirator) was used to remove the last traces of HCl. Deionized water (200 g) was then added and all the toluene was distilled off. The reaction mixture was neutralized to pH of 8 using 10% aqueous $NH_4OH$ and then diluted to 10% solids with isopropanol and water. (Final ratio of water/isopropanol was 70/30.) A sample of the resulting clear solution was analyzed by gas chromatography (after reacting with diazomethane) and was shown to contain approximately 3% unreacted alcohol, 85% monoester, 10% diester, and 2% triester.

The materials of the invention were diluted in water to 0.05% (500 ppm) and/or 0.01% (100 ppm), and the surface tension of the aqueous solution was measured using a Du Nouy tensiometer. Foam height was measured as volume in a graduated cylinder. Half-life time (t ½) is the time for half the liquid present in the foam to drain from the foam. The foam was generated by a wire wisk in a Hobart mixer. Thus, 200 mL of surfactant solution to be tested is placed in a bowl of Hobart Model N-50 mixer equipped with a wire wisk stirrer and stirred for 3 minutes at medium speed (setting 2=300 rpm). The foam produced was immediately transferred to a 4000 mL graduated cylinder for measuring foam height and half-life time.

Examples 36–39, Comparative Examples C6–C11

Using the synthetic procedure of Example 35, further examples (36–39) and Comparative Examples (C6–C11) were prepared as shown in Table 11.

TABLE 11

| Ex. | Fluorochemical Alcohol Used |
|---|---|
| 36 | $C_8F_{17}CH_2CH_2OH$ from Example 12, containing 44% linear material |
| 37 | $C_4F_9CH_2CH_2OH$ from Example 13 |
| 38** | $C_{10}F_{21}CH_2CH_2OH$ from Example 14, containing 65% linear material |
| 39 | $C_{10}F_{21}CH_2CH_2OH$ containing 40% linear material |
| C6 | $C_8F_{17}SO_2N(C_2H)CH_2CH_2OH$ N-ethyl perfluorooctane-sulfonamido ethanol (available from 3M) |
| C7** | $CnF2n+1CH_2CH_2OH$ <n> = 8 (available from DuPont) |
| C8* | $C_{10}F_{21}CH_2CH_2OH$ (available from Hoechst) |
| C9 | Zonyl FSP (ammonium salt of a fluorochemical phosphate mixture, available from DuPont) |
| C10 | Isomers of $C_6F_{11}$—$CF_2OCF(CF_3)CH_2OH$ as described in EP 314,380 |
| C11 | $CF_3(CF_2)_3OCF(CF_3)CF_2OCF(CF_3)CH_2OH$ |

*The ammonium salts of the phosphate esters were insoluble in water/isopropanol mixtures, even at very low concentrations.
**The reaction products had to be diluted to 5% solids in water/isopropanol prior to testing.

Example 40

Into a 500 mL three-necked flask fitted with a stirrer, a reflux condenser, and a thermometer, were placed 27.6 g (0.1 mole) of

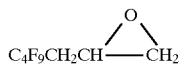

(as prepared in Example 26), 26.4 g (0.1 mole) of $C_4F_9CH_2CH_2OH$ (as prepared in Example 13) and 60 g benzene. Using a Dean Stark trap, 20 g benzene was distilled out. The reaction was cooled to about 40° C. under $N_2$, and then 0.25 g of boron trifluoride-etherate complex in ether was added. An immediate exotherm was observed of about 10° C. The reaction was heated at 75° C. under nitrogen for 5 hours, during which time a clear brown solution was formed. At room temperature, two liquid phases were obtained. The benzene layer containing the products was removed. The reaction mixture was analyzed by gas chromatography and found to contain about 15% unreacted $C_4F_9CH_2CH_2OH$ alcohol, about 70% monoadduct of 1 mole alcohol reacted with 1 mole epoxide, about 10% of diadduct of 1 mole alcohol reacted with 2 moles epoxide and about 3% of higher homologues. The reaction product was converted into a mixture of phosphate esters and their ammonium salts following the procedure described in Example 35.

Example 41

Following the procedure outlined in Example 25, the reaction product of 2 moles $C_4F_9CH_2CH_2SH$, as prepared in Example 16, and 1 mole of propargylalcohol, $CH{\equiv}CCH_2OH$, was prepared. The resulting adduct containing hydroxyl functionality was converted into the mixture of phosphate esters and their ammonium salts following the procedure described in Example 35.

Example 42

Into a 500 mL three-necked flask, fitted with a stirrer, a reflux condenser, and a thermometer were placed 6.7 g malic acid (0.05 mole), 26.4 g (0.1 mole) $C_4F_9CH_2CH_2OH$ as prepared in Example 13), 30 g methylisobutylketone and 0.2 g p-toluenesulfonic acid. The mixture was heated at reflux (about 98° C.) and H2O was collected in a Dean Stark trap. After 6 hours of reflux, 1.7 g $H_2O$ were trapped and the reaction stopped. All reaction solvent was removed. A diester alcohol of structure $C_4F_9CH_2CH_2OC(O)CH_2CH(OH)C(O)OCH_2CH_2C_4F_9$ was formed, which was subjected to the synthetic procedure followed in Example 35 to make ammonium salts of phosphate esters.

TABLE 12

| PRODUCT OF EXAMPLE | FOAM HEIGHT (VOLUME) 500 ppm | HALF-LIFE TIME (SEC) 500 ppm | SURFACE TENSION (dyne/cm) 500 ppm | SURFACE TENSION (dyne/cm) 500 ppm |
|---|---|---|---|---|
| 35 | 200 | <30 sec. | 17.5 | 18.1 |
| 36 | 400 | <30 sec. | 18.5 | 25.7 |
| 37 | 400 | <30 sec. | 33.3 | 44.9 |
| 38 | 400 | <30 sec. | 16.4 | 18.9 |
| 39 | 400 | <30 sec. | 18.7 | 24.3 |
| 40 | 1100 | 1 min. 15 sec. | 21.2 | 29.3 |
| 41 | 1000 | 50 sec. | 21.7 | 36.7 |
| 42 | 200 | <30 sec. | 21.3 | 28.5 |
| C6 | 1600 | 4 min 10 sec. | 17.2 | 18.5 |
| C7 | 200 | <30 sec. | 17.6 | 26.0 |
| C8 | insoluble | | | |
| C9 | 300 | <30 sec. | 18.0 | 26.6 |

TABLE 12-continued

| PRODUCT OF EXAMPLE | FOAM HEIGHT (VOLUME) 500 ppm | HALF-LIFE TIME (SEC) 500 ppm | SURFACE TENSION (dyne/cm) 500 ppm | SURFACE TENSION (dyne/cm) 500 ppm |
|---|---|---|---|---|
| C10 | 400 | <30 sec. | 20.4 | 26.8 |
| C11 | 300 | <30 sec. | 29.5 | 35.8 |

The data shows that the surfactants of this invention (compare, for example, Example 35 to Comparative Examples C6 and C7) have unexpected properties: low foaming and low surface tension in water. Compared to sulfonamido linking group containing derivatives (Comparative Example 6) our materials are low foaming, and compared to straight-chain derivatives (Comparative Example C7), the materials of this invention give lower surface tensions at equal perfluorinated chain lengths. The solubility of materials of this invention in aqueous systems is much better than their analogues (compare Examples 38 and 39 to Comparative Example C8. Compositions with 100% straight-chain materials give good properties but are usually poorly soluble at perfluorinated chain length of 8 carbons or more, and with 100% branched-chain materials (Comparative Example 10 and 11) are very soluble even at long carbon chains, e.g. $C_{10}$ or higher, but they are not as good for imparting lower surface tension. As Examples 35, 36, and 38 show, the preferable compositions contain from 45% to 95% straight perfluoroalkyl chains (5–55% branched) and more preferably contain from 50% to 85% straight-chain linear materials (15%–50% branched).

Example 43

Into a carefully dried 500 mL three-necked flask, fitted with a reflux condenser, thermometer, and a stirrer, were placed 46.4 g (0.1 mole) of $C_8F_{17}CH_2CH_2OH$ (as prepared in Example 12) and 20 g dry dioxane under nitrogen at room temperature. Then, 0.1 mole chlorosulfonic acid $ClSO_3H$ (12.7 g) was added dropwise over about 30 minutes. An exotherm and formation of HCl was observed. The reaction was heated at 70° C. under nitrogen until no more HCl could be detected (about 4 hours). A vacuum was then applied by aspirator to remove all residual HCl, and 200 g deionized water added and dioxane stripped off. The reaction mixture was neutralized to PH of 8 using 10% aqueous $NH_4H$ and then diluted to 10% solids with 70/30 water/isopropanol. A clear yellow solution resulted containing the ammonium salt of the fluorochemical sulfate, $C_8F_{17}CH_2CH_2OSO_3NH_4$.

Example 44, Comparative Examples C12, C13

Using the same procedure as in Example 43, Example 44 and Comparative Examples C12 and C13 were made (as shown in Table 13).

TABLE 13

| EX. | FLUOROCHEMICAL ALCOHOL USED |
|---|---|
| 44 | $C_8F_{17}CH_2CH_2OH$ from Example 12, containing 44% straight-chain material. |
| C12 | $C_8F_{17}SO_2N(C_2H)CH_2CH_2OH$ (available from 3M Company) |
| C13* | $C_nF_{2n+1}CH_2CH_2OH$ <n> = 8 (available from DuPont) |

*A dilution to 5% had to be made using 50/50 water/isopropanol as solvent mixture in order to obtain a clear solution.

The fluorochemical ammonium sulfate salts were tested as outlined under Example 35. The results of testing are shown in Table 14.

TABLE 14

| PRODUCT OF EXAMPLE | FOAM HEIGHT 500 ppm | t ½ sec 500 ppm | SURFACE TENSION (dyne/cm) | |
|---|---|---|---|---|
| | | | 500 ppm | 500 ppm |
| 43 | 400 | <30 sec | 19.5 | 22.8 |
| 44 | 800 | <30 sec. | 20.5 | 26.3 |
| C12 | 2200 | 6 min. 5 sec. | 17.1 | 18.2 |
| C13 | 400 | <30 sec. | 23.3 | 29.5 |

The data shows that the materials of this invention are generally low foaming and impart low surface tension.

Example 45

(See Example 1, U.S. Pat. No. 4,167,639)

Into a 500 mL three-necked flask, fitted with a condenser, a thermometer, and a stirrer, were placed 52.8 g (0.2 mole) of $C_4F_9CH_2CH_2OH$ as prepared in Example 13, 9.8 g maleic anhydride (0.1 mole) and 0.2 g sulfuric acid (95%). The reaction mixture was heated under nitrogen to 140° C. Water formed in the reaction was trapped in a Dean Stark collector. After about 6 hours of reaction, 1.7 mL water was obtained. The reaction mixture was a dark brown oil containing an unsaturated diester obtained from the ring opening and esterification reaction. The reaction mixture was cooled to room temperature, and 160 g deionized water, 80 g isopropanol and 19 g (0.1 mole) sodium metabisulfite ($Na_2S_2O_5$) was added. The two-phase mixture was degassed, then heated at reflux under nitrogen for 15 hours. A clear, one-phase, brown solution was obtained containing the diester sulfosuccinate sodium salt product NMR analysis confirmed the structure to be $C_4F_9CH_2CH_2OC(O)CH_2CH(SO_3Na)C(O)OCH_2CH_2C_4F_9$. The reaction mixture was diluted to 10% solids to give a final solvent ratio of water/isopropanol =65/35.

Example 46, Comparative Examples C14, C15

Example 46 and Comparative Examples C 14 and C 15 were prepared as described above in Example 44. The reactants are shown in Table 15.

TABLE 15

| EX. | FLUOROCHEMICAL ALCOHOL | RATIO FC ALCOHOL TO MALEIC ANHYDRIDE* | SULFONATING AGENT |
|---|---|---|---|
| 46 | $C_8F_{17}CH_2CH_2OH$ (Example 12) | 1:1 | $Na_2SO_3$ |
| C14 | $C_4F_9CH_2CH_2OH$ (available from Asahi Glass, 100% linear) | 2:1 | $Na_2S_2O_5$ |
| C15 | $C_nF_{2n+1}CH_2CH_2OH$ <n> = 8 (available from DuPont) | 1:1 | $Na_2SO_3$ |

*1:1 ratios yield monoester sulfosuccinate product; 2:1 ratios yield diestersulfosuccinate product.

The product of Examples 45, 46, and C14 and C15 were tested as described in Example 35. The results are shown in Table 16.

TABLE 16

| PRODUCT OF EXAMPLE | SURFACE TENSION (dynes/cm) | |
|---|---|---|
| | 500 ppm | 100 ppm |
| 45 | 17.7 | 24.2 |
| 46 | 20.1 | 22.0 |
| C14 | 21.7 | 30.5 |
| C15 | 20.5 | 29.5 |
| Hoe S-2407* | 38.8 | — |

*A sulfosuccinate diester sodium salt available from Hoechst.

The data shows that materials of this invention impart lower surface tension values in water than their straight-chain analogues.

Example 47

Surfactants can also be made by Michael addition of $R_{fsb}$-thiols of the invention to carbon-carbon double bonds containing an electron withdrawing group. Into a 500 mL three-necked flask fitted with a stirrer, thermometer, and reflux condenser, were placed 20.7 g (0.1 mole) of N-(3-sulfo-2,2-dimethylpropyl) acrylamide (AMPS), 50 g of dimethyl formamide (DMF) and 6.9 g (0.05 mole) of potassium carbonate. The mixture was stirred vigorously for 15 minutes. A clear, colorless solution resulted. Then 48.0 g (0.1 mole) of $C_8F_{17}CH_2CH_2SH$ and 0.01 g KOH were added. The reaction was heated at 70° C. for 8 hours. Gas chromatography analysis indicated that virtually no starting $R_{fsb}$-thiol was left. A clear solution was obtained at 10% dilution using water/isopropanol 65/35 as diluent. NMR analysis confirmed the structure to be $C_8F_{17}CH_2CH_2SCH_2CH_2C(O)NHCH_2C(CH_3)_2CH_2SO_3K$.

Examples 48–54, Comparative Examples C16, C17

Example 48–54 and Comparative Examples 16 and 17 were prepared as in Example 47. The reactants are shown in Table 17.

TABLE 17

| EXAMPLE | FLUOROCHEMICAL THIOL | UNSATURATED COMPOUND |
|---|---|---|
| 48 | $C_8F_{17}CH_2CH_2SH$ (Example 15) | AMPS - sodium salt |
| 49 | $C_8F_{17}CH_2CH_2SH$ (Example 15) | acrylic acid - sodium salt |
| 50 | $C_8F_{17}CH_2CH_2SH$ (Example 15) | Carbowax ™ 750 acrylate (CW750 is a methoxy polyethylene glycol available from Union Carbide) |
| 51 | $C_{10}F_{21}CH_2CH_2SH$ (Example 17) | Carbowax ™ 750 acrylate |
| 52 | $C_{10}F_{21}CH_2CH_2SH$ (Example 18) | Carbowax ™ 750 acrylate |
| 53 | $C_8F_{17}CH_2CH_2SH$ (Example 15) | dimethylamino ethyl acrylate, quaternized with diethylsulfate |
| 54 | $C_8F_{17}CH_2CH_2SH$ (Example 15) | dimethylamino ethyl acrylate, reacted with propane sultone |
| C16 | $C_{10}F_{21}CH_2CH_2SH$ (available from Atochem) | Carbowax ™ 750 acrylate |
| C17 | $C_nF_{2n+1}CH_2CH_2SH^*$ | Carbowax ™ 750 acrylate |

*Made from DuPont tetrahydroiodide following procedure of Example 15.

All fluorochemical surfactant materials of Examples 48–54 and Comparative Examples C16–C17 were tested as described in Example 35. The results are shown in Table 18.

TABLE 18

| PRODUCT OF EXAMPLE | SURFACE TENSION (dynes/cm) | |
|---|---|---|
| | 500 ppm | 100 ppm |
| 47 | 19.0 | 24.0 |
| 48 | 18.7 | 24.0 |
| 49 | 17.5 | 21.7 |
| 50 | 18.5 | 23.4 |
| 51 | 17.0 | 19.5 |
| 52 | 18.7 | 19.8 |
| 53 | 18.7 | 19.8 |
| 54 | 18.1 | 19.5 |
| C16 | insoluble | |
| C17 | 20.0 | 26.8 |

The data shows that products of the invention impart very low surface tensions, and have good solubility, in aqueous media up to a perfluorinated chain length of 10 carbons. These results also indicate that, for fluorochemical surfactant compositions of this invention, it is preferred that at least 40% of the compounds in the mixture contain straight-chain perfluoroalkyl group and more preferably at least 60% contain a straight-chain perfluoroaklyl group.

Example 55

In this example, the Michael addition of amines (or polyamines) to acrylates of this invention described. Into a 500 mL three-necked flask, fitted with a reflux condensor, a thermometer, and a stirrer, were placed 10.3 g (0.05 mole) AMPS, 80 g DMF and 3.6 g (0.025 mole) of $K_2CO_3$. The reaction was stirred vigorously at room temperature. A clear solution was obtained after 15 minutes. Then 25.9 g (0.05 mole) of $C_8F_{17}CH_2OCOCH=CH_2$, as prepared in Example 20, was added followed by 3 g (0.03 mole) of ethylene diamine (EDA). An exotherm of 10° C. was observed. The reaction was heated at about 50° C. for 3 hours. Gas chromatography indicated that essentially no reagents were left. The reaction mixture was diluted to 5% solids in water/isopropanol 50/50. The product mixture was tested as above in Example 35. NMR analysis confirmed the product structure to be $C_8F_{17}CH_2CH_2OC(O)CH_2CH_2NHCH_2CH_2NHCH_2CH_2C(O)NHCH_2 C(CH_3)_2CH_2SO_3K$.

Examples 56–65

Examples 56–65 were prepared as in Example 55. The reactants are shown in Table 19.

TABLE 19

| EX. | FLUOROCHEMICAL ACRYLATE A | AMINE B | COREAGENT C | MOLAR RATIO A/B/C |
|---|---|---|---|---|
| 56 | $C_8F_{17}CH_2CH_2OCOCH=CH_2$ (Example 20) | EDA[a] | AMPS-Na[+] | 1/1/1 |
| 57 | $C_8F_{17}CH_2CH_2OCOCH=CH_2$ (Example 20) | DMAPA[b] | AMPS-K[+] | 1/1/1 |
| 58 | $C_8F_{17}CH_2CH_2OCOCH=CH_2$ (Example 20) | EDA | CW750 acrylate | 1/1/1 |
| C59 | CnF2n + 1 $CH_2CH_2OCOCH=CH_2$ <n> = 8 (available from DuPont) | EDA | CW750 acrylate | 1/1/1 |
| 60 | $C_8F_{17}CH_2CH_2OCOCH=CH_2$ (Example 20) | EDA | acrylic acid K[+] | 1/1/1 |
| 61[c] | $C_8F_{17}CH_2CH_2OCOCH=CH_2$ (Example 20) | EDA | DMAEMA/DES | 1/1/1 |
| 62[f] | $C_8F_{17}CH_2CH_2OCOCH=CH_2$ (Example 20) | DMAPA | propane sultone | 1/1/2 |
| 63 | $C_4F_9CH_2CH_2OCOCH=CH_2$ (Example 21) | EDA | AMPS-Na[+] | 2/1/1 |
| 64 | $C_4F_9CH_2CH_2OCOCH=CH_2$ (Example 21) | DETA[d] | AMPS-Na[+] | 3/1/1 |
| 65 | $C_4F_9CH_2CH_2OCOCH=CH_2$ (Example 21) | TETA[e] | AMPS-Na[+] | 4/1/3 |

[a]EDA represents ethylene diamine
[b]DMAPA represents dimethylaminopropylamine
[c]DMAEMA/DES represents dimethylaminoethylacrylate, the tertiary nitrogen being quaternized with diethylsulfate (DES). Structure was confirmed by NMR to be $[C_8F_{17}CH_2CH_2OC(O)CH_2CH_2NHCH_2CH_2NHCH_2CH_2C(O)OCH_2CH_2N^+(CH_3)_2CH_2CH_3][CH_3CH_2SO^-_3]$
[d]DETA represents diethylene triamine
[e]TETA represents triethylene tetramine
[f]NMR confirmed structure to be

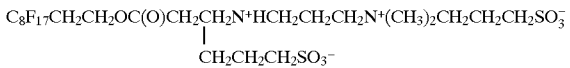

The above materials were tested as surfactants in water as in Example 35. The results are shown in Table 20.

TABLE 20

| PRODUCT OF EXAMPLE | SURFACE TENSION (dynes/cm) | |
|---|---|---|
| | 500 ppm | 100 ppm |
| 55 | 20.1 | 26.2 |
| 56 | 20.5 | 26.0 |

TABLE 20-continued

| PRODUCT | SURFACE TENSION (dynes/cm) | |
|---|---|---|
| OF EXAMPLE | 500 ppm | 100 ppm |
| 57 | 19.7 | 25.4 |
| 58 | 18.4 | 22.6 |
| C59 | 18.8 | 25.6 |
| 60 | 19.0 | 22.7 |
| 61 | 19.9 | 21.3 |
| 62 | 18.9 | 20.7 |
| 63 | 18.7 | 25.8 |
| 64 | 17.5 | 24.5 |
| 65 | 22.0 | 29.8 |

The data shown that materials of the invention give very good surfactant properties.

Example 66

Into a 500 mL three-necked flask, fitted with a stirrer, a thermometer, and a reflux condenser, were placed 15 g of $C_8F_{17}CH_2CH_2OCOCH=CH_2$ as prepared in Example 20, 35 g of Pluronic 44 diacrylate (the diacrylate ester of Pluronic 44, a diol containing block segments of oxyethylene and oxypropylene, available from BASF), 0.3 g n-octylmercaptan, 0.3 g AIBN and 35 g ethyl acetate. The reaction was warmed to about 40° C. and degassed three times using an aspirator vacuum. The reaction was heated at reflux (about 78° C.) under nitrogen and continued for 15 hours. Gas chromatography indicated that only traces of starting materials were left. Ethyl acetate was distilled off (aspirator vacuum) to yield a clear, viscous solution containing a fluorochemical nonionic surfactant of this invention.

Example 67

Into a 500 mL three-necked flask, fitted with a condenser, a thermometer, and a stirrer, was placed 20.7 g (0.1 mole) AMPS, 50 g DMF and 10.5 g (0.1 mole) diethanolamine under vigorous stirring at room temperature. After 15 minutes, a colorless solution was obtained. Then 9.6 g (0.02 mol) $C_8F_{17}CH_2CH_2SH$ (Example 15), was added together with 0.2 g AIBN. The reaction mixture was warmed to about 50° C. and degassed using an aspirator vacuum. The reaction mixture was heated at 85° C. under nitrogen for 15 hours. A clear yellow solution was obtained after filtration. NMR analysis confirmed the oligomeric product

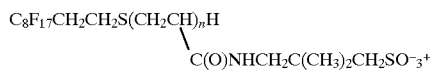

$NH_2(CH_2CH_2OH)_2$
where n has an average value of about 5.

Example 68

Using the same procedure as in Example 67 but using $C_8F_{17}CH_2CH_2I$ (Example 4), in place of the thiol, another adduct of the invention was prepared,

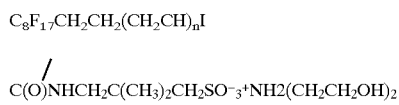

where n has an average value of about 5.

Example 69

Into a 500 mL three-necked flask of 500 mL, fitted with a reflux condenser, a thermometer, and a stirrer, were placed 23.3 g (0.05 mole) of $C_8F_{17}CH_2CH_2OH$ as prepared in Example 12, and 50 g methylethylketone (MEK). Then 20 g MEK was distilled out and trapped in a Dean Stark trap. The mixture was cooled to room temperature under nitrogen; then a Dewar condenser, filled with a dry ice/acetone mixture, was set up and 0.2 g boron trifluoride etherate complex in ether was added. Then 17.6 g (0.4 mole) of ethylene oxide were bubbled through the reaction solution over 2 hours and the reaction mixture heated at 35° to 40° C. Then the reaction was continued for 1 hour at 40° C. until no reflux of ethylene oxide was observed. The reaction mixture was heated at about 70° C. for 2 hours to yield a clear yellow-brown solution, containing a nonionic surfactant, $C_8F_{17}C_2H_4O(C_2H_4O)_nH$ where n has an average value of 8, as indicated by NMR and G/C analysis. All MEK was stripped off and the product was dissolved in a 70/30 mixture water/isopropanol at 10% solids. A clear yellow-brown solution resulted.

Example 70

Using the same procedure as in Example 69, a non-ionic surfactant was prepared using $C_8F_{17}CH_2CH_2SH$ (as prepared in Example 15) and a mixture of ethylene oxide and propylene oxide. The molar ratio $R_{fsh}$ thiol/ethylene oxide/propylene oxide was 1/12/3. NMR shows the product to be primarily $C_8F_{17}CH_2CH_2S(CH_2CH_2O)_{12}(CH_2CH(CH_3)O)_3H$ where the repeating units are randomly distributed.

Example 71

In a 500 mL three-necked flask, fitted with a reflux condenser, a stirrer, and a thermometer, were placed 10.2 g (0.1 mole) of N,N dimethyl amino propylamine and 50 g ethanol. The mixture was warmed to 50° C. and 47.6 g (0.1 mole) of

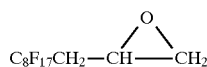

(as prepared in Example 27), were added over 30 minutes. The heating was continued at 60° C. for 2 hours. Gas chromatography indicated that all the fluorochemical epoxide was consumed. Then 0.2 mole (24.4 g) of propane sultone was added over 15 minutes. An exotherm of about 15° C. was observed. The heating was continued for 2 hours at 90° C. to yield a clear brown solution. The product was diluted to 10% solids using deionized water. The product was primarily

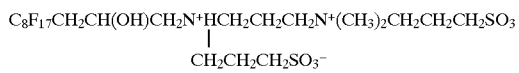

Example 72

Into a 500 mL three-necked flask, fitted with a stirrer, a reflux condenser, and a thermometer, were placed 4.9 g (0.05 mole) maleic anhydride, 10 g methyl ethyl ketone and 37.5 g (0.05 mole) of dry Carbowax 750 (a methoxypolyethylene glycol available from Union Carbide). The mixture was heated at 70° C. for 16 hours. After this period, no anhydride peak in the infrared spectrum could be detected. Then 24 g (0.05 mole) of $C_8F_{17}CH_2CH_2SH$, as prepared in Example 15, were added together with 0.4 g triethylamine catalyst. Heating was continued for 16 hours at 60° C. to yield a clear yellow-brown reaction solution. Gas chromatography indicated that only traces of thiol were left. Then the MEK was stripped off and the reaction product was dissolved in a 70/30 mixture of water/isopropanol at 10% solids. A clear solution containing a mixed anionic-nonionic surfactant was prepared by adding 4 g (0.05 mole) of a 50% NaOH solution in water. The product was a mixture of $C_8F_{17}CH_2CH_2SCH_2(CO_2Na)CH_2C(O)O(CH_2CH_2O)_nCH_3$ and $C_8F_{17}CH_2CH_2SCH_2(CH_2CO_2Na)C(O)O(CH_2CH_2O)_nCH_3$, where n has an average value of about 16.

The products of Examples 66 to 72 were tested as surfactants in water (at 500 ppm) as in Example 35. The results are shown in Table 21.

TABLE 21

| PRODUCT OF EXAMPLE | NATURE OF SURFACTANT | SURFACE TENSION (dynes/cm) |
|---|---|---|
| 66 | oligomeric nonionic | 32.1 |
| 67 | oligomeric anionic | 25.7 |
| 68 | oligomeric anionic | 23.5 |
| 69 | nonionic | 21.7 |
| 70 | nonionic | 23.1 |
| 71 | amphoteric | 17.5 |
| 72 | mixture of anionic + nonionic | 20.7 |

The data shows that surfactants of this invention exhibit very good aqueous surface tension properties, regardless of the nature of the polar group, i.e. ionic or nonionic, or of molecular weight.

Examples 73–77, Comparative Examples C60 and C61

Using the synthetic procedure of Example 35, several perfluoroalkyl group-containing phosphates having various percentages of $C_8$ straight-chain and branched perfluoroalkyl groups were synthesized from their alcohols. Their surface tensions in water were measured at 500 ppm and 100 ppm, and their solubilities in water at 500 ppm solids were noted. Alcohols used in Comparative Examples C60 and C61, purchased from Fluorochem Ltd., England, were 100% linear (i.e., straight-chain) $C_8$ tetrahydro alcohol and 100% branched $C_9$ tetrahydro alcohol, respectively. The alcohol mixtures used in Examples 73, 75 and 76 were blends of the alcohol used in Comparative Example C60 (100% linear or straight chain) and the alcohol used in Example 74 or Example 77 (both alcohols from Example 12).

Results are shown in Tables 22a–b.

TABLE 22a

| Example | Fluorochemical Alcohol Used |
|---|---|
| C60 | $C_8F_{17}CH_2CH_2OH$, 100% linear (available from Fluorochem Ltd., England) |
| 73 | $C_8F_{17}CH_2CH_2OH$, 80% linear (blend of alcohols from Ex. C60 and Ex. 74) |
| 74 | $C_8F_{17}CH_2CH_2OH$, 74% linear (alcohol semi-solid phase from Ex. 12) |
| 75 | $C_8F_{17}CH_2CH_2OH$, 65% linear (blend of alcohols from Ex. C60 and Ex. 77) |
| 76 | $C_8F_{17}CH_2CH_2OH$, 55% linear (blend of alcohols from Ex. C60 and Ex. 77) |
| 77 | $C_8F_{17}CH_2CH_2OH$, 44% linear (alcohol liquid phase from Ex. 12) |

TABLE 22a-continued

| Example | Fluorochemical Alcohol Used |
|---|---|
| C61 | $(CF_3)_2CF(CF_2)_6CH_2CH_2OH$, 0% linear (avail. from Fluorochem Ltd., England) |

TABLE 22b

| Product of Ex.: | % Linear Chains | Water Solub. (500 ppm) | Surface Tension (dynes/cm) at: 500 ppm | 100 ppm |
|---|---|---|---|---|
| C60 | 100 | Borderline | 17.6 | 21.7 |
| 73 | 80 | Soluble | 17.4 | 18.7 |
| 74 | 74 | Soluble | 17.6 | 18.1 |
| 75 | 65 | Soluble | 17.4 | 18.6 |
| 76 | 55 | Soluble | 18.0 | 20.0 |
| 77 | 44 | Soluble | 18.5 | 21.4 |
| C61 | 0 | Low | 18.8 | 23.5 |

The data in Tables 22a–b show a synergistic lowering of surface tension with the blends of $C_8$ straight-chain and branched perfluoroalkyl groups, with the synergism especially prominent at 100 ppm fluorochemical surfactant. Optimal surface tension lowering was obtained when at least 50%, but less than 100%, of the surfactant contained straight-chain perfluoroalkyl groups (Examples 73–76), with particularly good results when the ratio of straight-chain to branched-chain materials was within the range of about 65:35 (approximately 3:2) to about 80:20 (4:1). Also, improved water solubility of the phosphates was noted with the blends vs. 100% straight-chain or 100% branched perfluoroalkyl groups.

Examples 78–81, Comparative Examples C62 and C63

Using the synthetic procedure of Example 35, several perfluoroalkyl group-containing phosphates having various percentages of $C_{10}$ straight-chain and branched perfluoroalkyl groups were synthesized from their alcohols. Their surface tensions in water were measured at 500 ppm and 100 ppm, and their solubilities in water at 500 ppm solids were noted. Alcohols used in Comparative Examples C62 and C63, purchased from Fluorochem Ltd., England, were 100% linear (i.e., straight-chain) $C_{10}$ tetrahydro alcohol and 100% branched $C_{11}$ tetrahydro alcohol repectively. The alcohol mixtures used in Examples 78 and 80 were blends of the alcohol used in Comparative Example C62 (100% linear or straight chain) and the alcohol used in Example 79 (the alcohol from the solid phase of Example 14) or Example 81.

Results are shown in Tables 23a–b.

TABLE 23a

| Example | Fluorochemical Alcohol Used |
|---|---|
| C62 | $C_{10}F_{21}CH_2CH_2OH$, 100% linear (available from Fluorochem Ltd., England) |
| 78 | $C_{10}F_{21}CH_2CH_2OH$, 75% linear (blend of alcohols from Ex. C62 and Ex. 79) |
| 79 | $C_{10}F_{21}CH_2CH_2OH$, 63% linear (alcohol semi-solid phase from Ex. 14) |
| 80 | $C_{10}F_{21}CH_2CH_2OH$, 55% linear (blend of alcohols from Ex. C62 and Ex. 81) |
| 81 | $C_{10}F_{21}CH_2CH_2OH$, 40% linear (alcohol liquid phase from Ex. 14) |

TABLE 23a-continued

| Example | Fluorochemical Alcohol Used |
|---|---|
| C63 | $(CF_3)_2CF(CF_2)_6CH_2CH_2OH$, 0% linear (avail. from Fluorochem Ltd., England) |

TABLE 23b

| Product of Ex.: | % Linear Chains | Water Solub. (500 ppm) | Surface Tension (dynes/cm) at: 500 ppm | 100 ppm |
|---|---|---|---|---|
| C62 | 100 | Low | 19.2 | 25.7 |
| 78 | 75 | Soluble | 16.7 | 18.7 |
| 79 | 63 | Soluble | 16.6 | 18.1 |
| 80 | 55 | Soluble | 17.4 | 18.6 |
| 81 | 40 | Soluble | 18.5 | 20.0 |
| C63 | 0 | Low | 20.7 | 25.4 |

The data in Tables 23a–b show that, at 500 and 100 ppm concentrations in water, the phosphate surfactant blends containing greater than 50% but less than 100% straight-chain $C_{10}$ perfluoroalkyl groups (Examples 78–80) produce lower surface tensions than does the blend containing only 40% straight-chain perfluoroalkyl groups (Example 81), with optimal results achieved when the ratio of straight-chain to branched-chain materials was within the range of about 55:45 (approximately 1:1) to about 75:25 (3:1).

The $C_{10}$ phosphate blends in Tables 23a–b gave lower surface tensions than their $C_8$ counterparts in Tables 22a–b, showing the advantage of solubilizing the solubility $C_{10}$ chain.

Phosphates containing 100% of either straight-chain or branched $C_{10-11}$ perfluoroalkyl groups (Comparative Example C62 or C63 respectively) were too insoluble in water to be useful surfactants.

Examples 82–84, Comparative Examples C64 and C65

Using the synthetic procedure of Example 43, several perfluoroalkyl group-containing sulfates having various percentages of $C_8$ straight-chain and branched perfluoroalkyl groups were synthesized from their alcohols. Their surface tensions in water were measured at 500 ppm and 100 ppm, and their solubilities in water at 500 ppm solids were noted. Alcohols used in Comparative Examples C64 and C65, purchased from Fluorochem Ltd., England, were 100% linear (i.e., straight-chain) $C_8$ tetrahydro alcohol and 100% branched $C_9$ tetrahydro alcohol respectively. The alcohol mixture used in Examples 83 was a blend of the alcohol used in Comparative Example C64 (100% linear or straight chain) and the alcohol used in Example 84 (the alcohol from Example 12).

Results are shown in Tables 24a–b.

TABLE 24a

| Example | Fluorochemical Alcohol Used |
|---|---|
| C64 | $C_8F_{17}CH_2CH_2OH$, 100% linear (available from Fluorochem Ltd., England) |
| 82 | $C_8F_{17}CH_2CH_2OH$, 74% linear (alcohol mixture intermediate from Ex. 12) |
| 83 | $C_8F_{17}CH_2CH_2OH$, 60% linear (blend of alcohols from Ex. C64 and Ex. 84) |

TABLE 24a-continued

| Example | Fluorochemical Alcohol Used |
|---|---|
| 84 | $C_8F_{17}CH_2CH_2OH$, 44% linear (alcohol liquid phase from Ex. 12) |
| C65 | $(CF_3)_2CF(CF_2)_6CH_2CH_2OH$, 0% linear (avail. from Fluorochem Ltd., England) |

TABLE 24b

| Product of Ex.: | % Linear Chains | Water Solub. (500 ppm) | Surface Tension (dynes/cm) at: 500 ppm | 100 ppm |
|---|---|---|---|---|
| C64 | 100 | Borderline | 22.3 | 25.5 |
| 82 | 74 | Soluble | 19.2 | 22.8 |
| 83 | 60 | Soluble | 20.8 | 23.7 |
| 84 | 44 | Soluble | 21.9 | 24.5 |
| C65 | 0 | Low | 23.7 | 28.6 |

The data in Tables 24a–b show that, at 500 and 100 ppm concentrations in water, the sulfate surfactant blends containing greater than 50% but less than 100% straight-chain $C_8$ perfluoroalkyl groups (Examples 82 and 83) produce lower surface tensions than does the blend containing only 44% straight-chain perfluoroalkyl groups (Example 84), with optimal results obtained near a ratio of 74:26 (approximately 3:1). Sulfates containing 100% of either straight-chain $C_8$ or branched $C_{8-9}$ perfluoroalkyl groups (Comparative Example C64 or C65, respectively) were too insoluble in water to be useful surfactants.

Examples 85 and 86, Comparative Examples C66 and C67

Using the synthetic procedure of Example 55 to synthesize Michael adducts having the composition shown in Example 58, perfluoroalkyl group-containing acrylates having various percentages of $C_8$ straight-chain and branched perfluoroalkyl groups were reacted with ethylene diamine (EDA) and the acrylate of Carbowax™ 750 (methoxy-terminated 750 molecular weight polyoxyethylene) in a 1:1:1 molar ratio. Their surface tensions in water were measured at 500 ppm and 100 ppm, and their solubilities in water at 500 ppm solids were noted. Acrylates used in Comparative Examples C66 and C67, purchased from Fluorochem Ltd., England, were derived from 100% linear (i.e., straight-chain) $C_8$ tetrahydro alcohol and 100% branched $C_9$ tetrahydro alcohol respectively. The Michael adduct used in Examples 85 was made from the 74% straight-chain perfluoroalkyl acrylate prepared in Example 20 (made in turn from the alcohol mixture prepared in Example 12). The Michael adduct used in Example 86 was made by reacting EDA and the acrylate of Carbowax™ 750 with an perfluoroalkyl acrylate, which in turn was made by reacting acrylic acid with a blend of the 100% straight-chain $C_8F_{17}CH_2CH_2OH$ alcohol available from Fluorochem and the 44% linear $C_8F_{17}CH_2CH_2OH$ alcohol from the liquid phase isolated in Example 12.

Results are shown in Tables 25a–b.

TABLE 25a

| Example | Fluorochemical Alcohol Used |
|---|---|
| C66 | $C_8F_{17}CH_2CH_2OH$, 100% linear (available from Fluorochem Ltd., England) |
| 85 | $C_8F_{17}CH_2CH_2OH$, 74% linear (alcohol mixture intermediate from Ex. 12) |
| 86 | $C_8F_{17}CH_2CH_2OH$, 65% linear (blend of alcohols from Ex. C60 and Ex. 77) |
| C67 | $(CF_3)_2CF(CF_2)_6CH_2CH_2OH$, 0% linear (avail. from Fluorochem Ltd., England) |

TABLE 25b

| Product of Ex.: | % Linear Chains | Water Solub. (500 ppm) | Surface Tension (dynes/cm) at: 500 ppm | 100 ppm |
|---|---|---|---|---|
| C66 | 100 | Borderline | 18.6 | 25.0 |
| 85 | 74 | Soluble | 18.4 | 22.1 |
| 86 | 65 | Soluble | 18.6 | 23.7 |
| C67 | 0 | Low | 20.6 | 28.1 |

The data in Tables 25a–b show that, at 100 ppm concentration in water, the Michael adduct surfactant blends containing greater than 50% but less than 100% straight-chain $C_8$ perfluoroalkyl groups (Examples 85 and 86) produce lower surface tensions than does the Michael adduct containing 100% of straight-chain $C_8$ perfluoroalkyl groups (Comparative Example C66), with optimal results occuring at ratios of straight-chain to branch-chain materials within the range from about 65:35 (approximately 3:1) to about 74:26 (approximately 3:1). The Michael adduct containing 100% of branched C9 perfluoroalkyl groups (Comparative Example C67) was too insoluble in water to be a useful surfactant.

Example 87, Comparative Examples C68 and C69

Using the synthetic procedure of Example 71 to synthesize propane sultone adducts, perfluoroalkyl group-containing epoxides having various percentages of $C_8$ straight-chain and branched perfluoroalkyl groups were reacted with N,N-dimethylaminopropylamine and propane sultone at a 1:1:2 molar ratio. Their surface tensions in water were measured at 500 ppm and 100 ppm, and their solubilities in water at 500 ppm solids were noted. Epoxides used in Comparative Examples C68 and C69, purchased from Fluorochem Ltd., England, were derived from 100% straight-chain (i.e., linear) $C_8$ tetrahydro alcohol and 100% branched $C_9$ tetrahydro alcohol respectively. The propane sultone adduct used in Examples 85 was made from the 74% straight-chain perfluoroalkyl epoxide prepared in Example 27.

Results are shown in Tables 26a–b.

TABLE 26a

| Example | Fluorochemical Epoxide Used |
|---|---|
| C68 | $C_8F_{17}CH_2CHCH_2$, 100% linear (available from Fluorochem Ltd., England) |
| 87 | $C_8F_{17}CH_2CHCH_2$, 74% linear (epoxide intermediate from Ex. 27) |
| C69 | $(CF_3)_2CF(CF_2)_6CH_2CHCH_2$, 0% linear (avail. from Fluorochem Ltd., England) |

TABLE 26b

| Product of Ex.: | % Linear Chains | Water Solub. (500 ppm) | Surface Tension (dynes/cm) at: 500 ppm | 100 ppm |
|---|---|---|---|---|
| C68 | 100 | Low | 20.3 | 26.5 |
| 87 | 74 | Soluble | 17.8 | 19.8 |
| C69 | 0 | Low | 22.8 | 31.2 |

The data in Tables 26a–b show that the propane sultone adduct containing 74% straight-chain $C_8$ perfluoroalkyl groups (Example 87) shows better water solubility than does the propane sultone adduct containing either 100% of straight-chain $C_8$ perfluoroalkyl groups (Comparative Example C68) or 100% of branched $C_9$ perfluoroalkyl groups (Comparative Example C69), with optimal results occuring near a ratio of straight-chain to branched-chain material of about 74:26 (approximately 3:1). The mixed chain adduct in Example 87 exhibits good surface tension reduction of water.

Comparative Example C70

A polyacrylate copolymer emulsion containing 100% straight-chain perfluoroalkyl groups was made using the following polymerization procedure.

In a 250 mL bottle were charged 47.5 g of $C_8F_{17}CH_2CH_2OC(O)CH=CH_2$ (100% straight-chain perfluoroalkyl group-containing acrylate monomer, available from Fluorochem Ltd., England), 2.5 g of isobutyl methacrylate, 93.3 g of deionized water, 23 g of acetone, 1.25 g of Ethoquad™0 18/25 surfactant (available from Akzo Nobel Chemicals, Chicago, Ill.), 0.12 g of Sipomer™ Q-6 cationic monomer (available from Rhone-Poulenc, North Americal Chemicals, Cranbury, N.J.), 0.1 g of Vazo™ V-50 initiator [2,2'-azobis(2-amidinopropane) hydrochloride] (available from Wako Chemicals USA, Inc., Richmond, Va.), and 0.25 g of tert-dodecyl mercaptan. The bottle and contents were degassed by vacuum aspiration followed by pressurization with nitrogen. The polymerization was run for 16 hours at 70° C. under nitrogen, giving an emulsion with about 30% (wt) solids.

Examples 88–91 and Comparative Example C71

Polyacrylate copolymer emulsions containing varying percentages of straight-chain and branched perfluoroalkyl groups was made using the same polymerization procedure as described in Comparative Example C70 except that the following fluoroalkyl monomers were used in place of the 100% straight-chain perfluoroalkyl group-containing acrylate monomer:

| Example | Perfluoroalkyl Group-Containing Acrylate Monomer |
|---|---|
| 88 | $C_8F_{17}CH_2CH_2OC(O)CH=CH_2$, 85% straight-chain $R_f$ (blend of acrylate monomers from Comparative Example C70 and Example 89) |
| 89 | $C_8F_{17}CH_2CH_2OC(O)CH=CH_2$, 77% straight-chain $R_f$ (acrylate monomer from Example 20) |
| 90 | $C_8F_{17}CH_2CH_2OC(O)CH=CH_2$, 65% straight-chain $R_f$ (blend of acrylate monomers from Example 89 and Example 91) |
| 91 | $C_8F_{17}CH_2CH_2OC(O)CH=CH_2$, 44% straight-chain $R_f$ (acrylate monomer made from the tetrahydro alcohol of Example 12, using the procedure described in Example 20) |

-continued

| Example | Perfluoroalkyl Group-Containing Acrylate Monomer |
|---|---|
| C71 | $(CF_3)_2CF(CF_2)_6CH_2CH_2OC(O)CH=CH_2$, 0% straight-chain $R_f$ (available from Fluorochem Ltd., England) |

The quality of polyacrylate copolymer emulsions made in Examples 88–91 (microemulsions) was clearly superior to the quality of polyacrylate copolymer emulsions made in Comparative Examples C70–C71 (milky emulsions).

Examples 92–95 and Comparative Examples C72–C73

The acrylate copolymer emulsions made in Examples 88–91 and Comparative Examples C70–C71, with varying percent straight-chain perfluoroalkyl groups (% SC), were applied to style #407 cotton fabric using the Padding Application Procedure, and the treated fabrics were evaluated for repellency using the Spray Rating Test (SR) and the Oil Repellency Test (OR), initially and after five launderings or after one dry cleaning. Results are set forth in Table 27.

TABLE 27

| | Acrylate Polymer: | | Initial: | | 5 × Laundered: | | Dry Cleaned: | |
|---|---|---|---|---|---|---|---|---|
| Ex. | Ref. | % SC | OR | SR | OR | SR | OR | SR |
| C72 | C70 | 100 | 4 | 80 | 2 | 50 | 3 | 70 |
| 92 | 88 | 85 | 5 | 90 | 3 | 70 | 4 | 70 |
| 93 | 89 | 77 | 5 | 90 | 3 | 70 | 4 | 70 |
| 94 | 90 | 65 | 4 | 80 | 2 | 50 | 4 | 70 |
| 95 | 91 | 44 | 3 | 70 | 2 | 50 | 3 | 50 |
| C73 | C71 | 0 | 3 | 70 | 1 | 50 | 2 | 50 |

The data in Table 27 show that acrylate copolymers made from monomers containing mixtures of straight-chain and branched chain perfluoroalkyl groups show improved oil repellency and water spray rating when compared to acrylate copolymers made from monomers containing 100% straight-chain or branched chain perfluoroalkyl groups, initially and after either laundering or dry cleaning. Best results were achieved when straight-chain perfluoroalkyl groups were incorporated at levels of at least 50%.

Examples 96–99 and Comparative Examples C74–C75

Various fluorochemical urethane oligomers were prepared by reacting $OCNC_6H_4CH_2[C_6H_3(NCO)]_nCH_2C_6H_4NCO$ polyisocyanate with 2-butanone oxime and with the perfluoroalkyl tetrahydroalcohols listed below, using the synthetic and emulsifying procedures set forth earlier in Example 30:

| Example | Perfluoroalkyl Group-Containing Tetrahydro Alcohol |
|---|---|
| C74 | $C_8F_{17}CH_2CH_2OH$, 100% straight-chain $R_f$ (available from Fluorochem Ltd., England) |
| 96 | $C_8F_{17}CH_2CH_2OH$, 85% straight-chain $R_f$ (blend of tetrahydro alcohols from Comparative Example C74 and Example 97) |
| 97 | $C_8F_{17}CH_2CH_2OH$, 74% straight-chain $R_f$ (a tetrahydro alcohol from Example 12) |
| 98 | $C_8F_{17}CH_2CH_2OH$, 65% straight-chain $R_f$ (blend of tetrahydro alcohols from Example 97 and Example 99) |
| 99 | $C_8F_{17}CH_2CH_2OH$, 44% straight-chain $R_f$ (a tetrahydro alcohol from Example 12) |
| C75 | $(CF_3)_2CF(CF_2)_6CH_2CH_2OH$, 0% straight-chain $R_f$ (available from Fluorochem Ltd., England) |

The quality of the fluorochemical urethane oligomer emulsions prepared in Comparative Examples C74 and C75 was inferior to those emulsions made in Examples 96–99, probably due to a lower solubility of the urethane oligomers in ethyl acetate which made emulsification far more difficult.

The fluorochemical urethane oligomer emulsions made in Examples 96–99 and in Comparative Examples C74–C75 were applied to style #407 cotton fabric using the Padding Application Procedure and were evaluated for repellency using the Oil Repellency Test and the Spray Rating Test, initially and after laundering or dry cleaning. Test results are set forth in Table 28.

TABLE 28

| Urethane Oligomer: | | Initial: | | 5 × Laundered: | | Dry Cleaned: | |
|---|---|---|---|---|---|---|---|
| Ex. | % SC | OR | SR | OR | SR | OR | SR |
| C74 | 100 | 3 | 100 | 2 | 70 | 2 | 70 |
| 96 | 85 | 3 | 100 | 3 | 90 | 3 | 80 |
| 97 | 74 | 3 | 100 | 3 | 80 | 2 | 80 |
| 98 | 65 | 2 | 100 | 2 | 80 | 2 | 80 |
| 99 | 44 | 2 | 100 | 1 | 70 | 1 | 70 |
| C75 | 0 | 2 | 90 | 1 | 70 | 1 | 70 |

The data in Table 28 show that the urethane oligomers made from mixed straight-chain and branched perfluoroalkyl groups and having at least 65% straight-chain groups shows improved spray rating and slightly better oil resistance after laundering or dry cleaning.

Example 100

A fluorochemical carbodiimide oligomer was prepared by reacting $OCNC_6H_4CH_2[C_6H_3(NCO)]_nCH_2C_6H_4NCO$ polyisocyanate with a perfluoroalkyl tetrahydroalcohol having 74% straight-chain perfluoroalkyl groups using the following procedure.

Into a 3-necked flask equipped with a stirrer, heating mantle, condenser and thermometer were charged 75 g (0.3 mol) of $OCNC_6H_4CH_2[C_6H_3(NCO)]_nCH_2C_6H_4NCO$ polyisocyanate (average value of n=0.7, available from Upjohn Co., Kalamazoo, Mich.) and 40 g of dry ethyl acetate. The mixture was heated to 65° C. with mixing under a nitrogen atmosphere. Then, using an addition funnel, a solution consisting of 92.8 g (0.2 mol) of the perfluoroalkyl tetrahydroalcohol prepared in Example 12 in 50 g of dry ethyl acetate was added over a 3 hour period, maintaining the reaction temperature at 65° C. After a 1 hour reaction time, 1 drop (0.03 mL) of dibutyltin dilaurate was added, and the reaction was cooled for an additional 3 hours at 70° C. under nitrogen. A clear solution was obtained.

To this urethane reaction product containing unreacted isocyanate was added 6 g of camphene phospholene oxide catalyst and the reaction temperature was increased to 80° C. (still under nitrogen). Gentle evolution of carbon dioxide was observed, suggesting carbodiimide formation. The reaction was allowed to run for 16 hours at 80° C., after which a clear solution resulted. Infrared analysis indicated that all residual isocyanate groups from the isocyanate-alcohol reaction had reacted with each other to form carbodiimide groups.

The resulting carbodiimide oligomer solution in ethyl acetate was emulsified in water using the same procedure as described in Example 30.

Comparative Examples C76 and C77

The same reaction and emulsifying procedures were conducted as described in Example 100 except that perfluoroalkyl tetrahydroalcohol having 100% straight-chain perfluoroalkyl groups (available from Fluorochem Ltd.) and perfluoroalkyl tetrahydroalcohol having 0% straight-chain perfluoroalkyl groups ($(CF_3)_2CF(CF_2)_6CH_2CH_2OH$, available from Fluorochem Ltd.) were substituted for the perfluoroalkyl tetrahydroalcohol having 74% straight-chain perfluoroalkyl groups for Comparative Examples C76 and C77 respectively. In both bases, the ethyl acetate solutions of the urethane intermediates and the carbodimide oligomers were hazy, indicating poor solubility relative to the urethane intermediate and carbodiimide oligomer prepared in Example 100.

The fluorochemical carbodiimide oligomer emulsions made in Example 100 and Comparative Examples C76–C77 were applied to style #407 cotton fabric using the Padding Application Procedure and were evaluated for repellency using the Oil Repellency Test and the Spray Rating Test, both initially and after laundering or dry cleaning. Test results are set forth in Table 29.

TABLE 29

| Carbodiimide Oligomer: | | Initial: | | 5 × Laundered: | | Dry Cleaned: | |
|---|---|---|---|---|---|---|---|
| Ex. | % SC | OR | SR | OR | SR | OR | SR |
| C76 | 100 | 4 | 70 | 2 | 50 | 1 | 0 |
| 100 | 74 | 5 | 80 | 3 | 70 | 2 | 50 |
| C77 | 0 | 3 | 70 | 1 | 50 | 0 | 0 |

The data in Table 29 show in all cases that carbodiimide oligomers made from mixed straight-chain and branched perfluoroalkyl groups exhibited improved spray rating and better oil repellency, both initially and after laundering or dry cleaning.

Example 101

A fluorochemical ester oligomer was prepared by reacting adipic acid with a perfluoroalkyl tetrahydroalcohol/epichlorohydrin adduct having 74% straight-chain perfluoroalkyl groups.

The precursor perfluoroalkyl tetrahydroalcohol/epichlorohydrin adduct was first prepared using the following procedure. Into a 500 mL 3-necked flask equipped with a stirrer, heating mantle, condensor and thermometer were charged 92.8 g (0.2 mol) of the perfluoroalkyl tetrahydroalcohol previously prepared in Example 12 and 20 g of toluene under a nitrogen blanket. The content was warmed to about 50° C., then 21 g (0.22 mol) of epichlorohydrin was added, followed by 1 g of anhydrous $SnCl_4$ catalyst, resulting in an exotherm. The contents were allowed to react for 3 hours at 50° C. under nitrogen. A clear brown solution resulted, which, when analyzed by gas chromatography, showed the reaction product to consist of $C_8F_{17}CH_2CH_2[OCH_2CH(CH_2Cl)]_nOH$, with 28.7% of n=0 (starting alcohol), 53.5% of n=1, 10.1% of n=2, 3.2% of n=3 and 4.5% of n≧4.

The fluorochemical ester oligomer was prepared by esterifying the precursor perfluoroalkyl tetrahydroalcohol/epichlorohydrin adduct with adipic acid using the following procedure. Toluene was stripped from the epichlorohydrin adduct solution at 90°–110° C. and aspirator vacuum of approximately 20 torr. Then 80 g of methyl isobutyl ketone (MIBK), 15.6 g (0.1 mol) of adipic acid and 0.52 g of p-toluenesulfonic acid catalyst were added, and the reaction mixture was heated to reflux, removing the water of reaction via azeotropic distillation with a Dean-Stark trap. After 6 hours, the reaction mixture had reached 120° C. and no further water was collected, so the reaction was stopped.

The resulting ester oligomer solution in MIBK was emulsified in water using the same procedure as described in Example 30.

Comparative Examples C78 and C79

The same reaction and emulsifying procedures were conducted as described in Example 101 except that perfluoroalkyl tetrahydroalcohol having 100% straight-chain perfluoroalkyl groups (available from Fluorochem Ltd.) and perfluoroalkyl tetrahydroalcohol having 0% straight-chain perfluoroalkyl groups ($(CF_3)_2CF(CF_2)_6CH_2CH_2OH$, available from Fluorochem Ltd.) were substituted for the perfluoroalkyl tetrahydroalcohol having 74% straight-chain perfluoroalkyl groups for Comparative Examples C78 and C79 respectively.

The fluorochemical ester oligomer emulsions made in Example 101 and Comparative Examples C78–C79 were applied to style #407 cotton fabric using the Padding Application Procedure and were evaluated for repellency using the Oil Repellency Test and the Spray Rating Test, both initially and after laundering or dry cleaning. Test results are set forth in Table 30.

TABLE 30

| Carbodiimide Oligomer: | | Initial: | | 5 × Laundered: | | Dry Cleaned: | |
|---|---|---|---|---|---|---|---|
| Ex. | % SC | OR | SR | OR | SR | OR | SR |
| C78 | 100 | 6 | 50 | 1 | 0 | 0 | 0 |
| 101 | 74 | 7 | 60 | 2 | 50 | 1 | 0 |
| C79 | 0 | 4 | 0 | 0 | 0 | 0 | 0 |

The data in Table 30 show that ester oligomers made from mixed straight-chain and branched perfluoroalkyl groups showed improved spray rating and oil repellency, both initially and after laundering. The ester oligomers containing all straight-chain or branched perfluoroalkyl groups showed no oil repellency after dry cleaning.

Various modifications and variations of this invention will become apparent to those skilled in the art without departing from the scope and spirit of this invention.

What is claimed is:

1. A method for treating a substrate, comprising the steps of:
   providing a substrate;
   providing a polymer comprising a plurality of pendant saturated perfluoroalkyl groups, wherein some of said perfluoroalkyl groups are straight chain and some are branched chain; and
   applying the polymer to the substrate;
   wherein about 65 to about 85% of the perfluoroalkyl groups are straight chain and about 15 to about 35% of the perfluoroalkyl groups are branched chain.

2. The method of claim 1, wherein the perfluoroalkyl groups are bonded to the polymer chain by way of at least one alkylene moiety.

3. The method of claim 1, wherein the perfluoroalkyl groups are bonded to the polymer chain directly.

4. The method of claim 1, wherein the polymer is selected from the group consisting of:
 polyurethanes, polyamides, polyolefins, polycarbodiimides, and polyethers.

5. The method of claim 1, wherein the polymer is a polyurethane.

6. The method of claim 1, wherein the polymer is an oligomeric urethane.

7. The method of claim 6, wherein the urethane has blocked isocyanate groups.

8. The method of claim 1, wherein, on average, about 5 to about 95 mole percent of the interpolymerized or repeating units in the polymer contain pendant perfluoroalkyl groups.

9. The method of claim 1, wherein the substrate is a fibrous substrate.

10. The method of claim 9, wherein the substrate is a carpet.

11. The method of claim 1, wherein the substrate is selected from the group consisting of glass, metal, plastic, paper, and ceramic substrates.

12. A method for treating a substrate, comprising the steps of:
 providing at least one monomer of the formula $R_{fsb}$—(Z), wherein Z is a polymerizable moiety, wherein $R_{fsb}$ represents a plurality of perfluoroalkyl groups pendant from Z, and wherein some of said perfluoroalkyl groups are straight chain and some are branched chain;
 providing a substrate;
 applying the at least one monomer to the substrate; and
 polymerizing the monomer on the substrate to produce a polymer.

13. The method of claim 12, wherein about 5% to about 95% of the perfluoroalkyl groups in the polymer are straight chain and about 5% to about 95% of the perfluoroalkyl groups in the resulting polymer are branched chain.

14. The method of claim 12, wherein about 60 to about 90% of the perfluoroalkyl groups in the resulting polymer are straight chain and about 10 to about 40% of the perfluoroalkyl groups in the resulting polymer are branched chain.

15. The method of claim 12, wherein about 65 to about 85% of the perfluoroalkyl groups in the resulting polymer are straight chain and about 15 to about 35% of the perfluoroalkyl groups in the resulting polymer are branched chain.

16. The method of claim 12, wherein $R_{fsb}$—(Z) is formed by a condensation reaction between a tetrahydroalcohol and a precursor monomer.

17. The method of claim 16, wherein the tetrahydroalcohol has the formula $R_f$—$C_2H_4OH$, wherein $R_f$ is a perfluoroalkyl moiety.

18. The method of claim 12, wherein $R_{fsb}$—(Z) is formed by a condensation reaction between a precursor monomer and a carboxylic acid or a metal or ammonium salt thereof.

19. The method of claim 12, wherein $R_{fsb}$—(Z) is formed by the reaction between a precursor monomer and a metal salt of a carboxylic acid having the formula $R_f$—$COOM_{1/v}$, wherein M is a metal atom having a valence v.

20. The method of claim 19, wherein M is K or Na.

21. The method of claim 12, wherein said polymer is an ester.

22. The method of claim 12, wherein said polymer is an amide.

23. The method of claim 22, wherein Z is $CONR_1R_2$, and wherein $R^1$ and $R^2$ are the same or different and are alkyl, aryl, or alkylaryl groups.

24. The method of claim 12, wherein Z is $COM_{1/v}$, wherein M is a metal atom having a valence v.

25. The method of claim 24, wherein M is K or Na.

26. The method of claim 12, wherein Z has the formula COOG, wherein G is selected from the group consisting of $NH_4$ and $NR^1R^2$, and wherein $R_1$ and $R^2$ are alkyl, aryl, or alkylaryl.

27. The method of claim 12, wherein Z is a sulfonic acid, or a metal or ammonium salt thereof.

28. The method of claim 12, wherein Z is $CH_2OH$.

29. The method of claim 12, wherein Z is selected from the group consisting of $CH_2OCOCR_4$=$CH_2$ and $CH_2OCOCF_2SF_5$.

30. The method of claim 12, wherein $R_{fsb}$—(Z) is a vinyl ether.

31. The method of claim 30, wherein Z is —$CH_2$—O—$CH_2CHCH_2$.

32. The method of claim 12, wherein each $R_{fsb}$—Z comprise a perfluoroalkyl group, a halogen atom selected from the group consisting of I, Cl, or Br, and an alkylene group linking the perfluoroalkyl group and the halogen atom, and wherein the alkylene linking group contains 1 to 20 carbon atoms.

33. A method for making a polymer, comprising the steps of:
 providing first and second monomers, wherein the first monomer comprises a straight chain perfluoroalkyl group, and wherein the second monomer comprises a branched chain perfluoroalkyl group; and
 copolymerizing the first and second monomers to produce a copolymer having both branched and straight chain perfluoroalkyl groups.

34. The method of claim 33, wherein about 60 to about 90% of the perfluoroalkyl groups on the copolymer are straight chain and about 10 to about 40% of the perfluoroalkyl groups on the polymer are branched chain.

35. The method of claim 33, wherein about 65 to about 85% of the perfluoroalkyl groups on the copolymer are straight chain and about 15 to about 35% of the perfluoroalkyl groups on the polymer are branched chain.

36. The method of claim 33, wherein the first monomer has only straight chain perfluoroalkyl groups, and wherein the second monomer has only branched chain perfluoroalkyl groups.

37. The method of claim 36, wherein the ratio of said first monomer to said second monomer is within the range of about 1.5:1 to about 9:1.

38. The method of claim 36, wherein the ratio of said first monomer to said second monomer is within the range of about 2:1 to about 6:1.

39. The method of claim 33, wherein at least one of said first and second monomers is selected from the group consisting of urethanes and carbodiimides.

40. A method for making a polymer, comprising the steps of:
 providing a monomer containing both branched and straight chain perfluoroalkyl groups; and
 polymerizing the monomer to produce a polymer having both branched and straight chain perfluoroalkyl groups.

41. The method of claim 40, wherein about 60 to about 90% of the perfluoroalkyl groups on the polymer are straight chain and about 10 to about 40% of the perfluoroalkyl groups on the polymer are branched chain.

42. The method of claim 40, wherein about 65 to about 85% of the perfluoroalkyl groups on the polymer are straight chain and about 15 to about 35% of the perfluoroalkyl groups on the polymer are branched chain.

* * * * *

UNITED STATES PATENT AND TRADEMARK OFFICE
CERTIFICATE OF CORRECTION

PATENT NO. : 5,852,148
DATED : December 22, 1998
INVENTOR(S) : Behr et al.

It is certified that error appears in the above-identified patent and that said Letters Patent is hereby corrected as shown below:

Column 15,
Line 31, after "epoxy", insert thereof -- compound --.
Line 53, delete "1∫27" and insert in place thereof -- 1-27 --.

Column 16,
Line 9, delete "1" at the end of example 5 and insert in place thereof -- I --.
Line 42, delete "hexametboxymethyl" and insert in place thereof
-- hexamethoxymethyl --.
Line 44, before "perfluoroctyl" insert thereof -- of --.

Column 21,
Line 51, delete "POC113" and insert in place thereof -- POC13 --.

Column 22,
Line 51, delete "$C_8F_{17}SO_2N(C_2H)CH_2CH_2OH$" and insert in place thereof
-- $C_8F_{17}SO_2N(C_2H_5)CH_2CH_2OH$ --.

Column 24,
Line 22, after "their" insert thereof -- straight-chain --.
Line 25, after "and" insert thereof -- compositions --.
Line 63, delete "$C_8F_{17}SO_2N(C_2H)CH_2CH_2OH$" and insert in place thereof
-- $C_8F_{17}SO_2N(C_2H_5)CH_2CH_2OH$ --.

Column 28,
Line 2, delete "$C_8F_{17}CH_2OCOCH=CH_2$" and insert in place thereof
-- $C_8F_{17}CH_2CH_2OCOCH=CH_2$ --.

Column 31,
Line 46, delete "Thealcohol" and insert in place thereof -- The alcohol --.

Column 32,
Line 48, delete "repectively" and insert in place thereof -- respectively --.

Column 36,
Line 33, delete "()" after ™.

UNITED STATES PATENT AND TRADEMARK OFFICE
CERTIFICATE OF CORRECTION

PATENT NO. : 5,852,148
DATED : December 22, 1998
INVENTOR(S) : Behr et al.

It is certified that error appears in the above-identified patent and that said Letters Patent is hereby corrected as shown below:

Column 39,
Line 19, delete "carbodimide" and insert in place thereof -- carbodiimide --.
Line 67, delete "n $\geqq$ 4" and insert in place thereof -- n $\geq$ 4 --.

Signed and Sealed this

Tenth Day of September, 2002

Attest:

JAMES E. ROGAN
Attesting Officer  Director of the United States Patent and Trademark Office